United States Patent
Gangwish et al.

(10) Patent No.: US 11,793,716 B2
(45) Date of Patent: *Oct. 24, 2023

(54) MUSCLE OPTIMIZATION DEVICE AND METHOD

(71) Applicant: Genovus Biotechnologies Inc., Louisville, CO (US)

(72) Inventors: Kimberly S. Gangwish, Louisville, CO (US); Garret Moddel, Boulder, CO (US)

(73) Assignee: Genovus Biotechnologies Inc., Louisville, CO (US)

( * ) Notice: Subject to any disclaimer, the term of this patent is extended or adjusted under 35 U.S.C. 154(b) by 10 days.

This patent is subject to a terminal disclaimer.

(21) Appl. No.: 17/556,314

(22) Filed: Dec. 20, 2021

(65) Prior Publication Data

US 2022/0110828 A1 Apr. 14, 2022

Related U.S. Application Data

(63) Continuation of application No. 16/395,017, filed on Apr. 25, 2019, now Pat. No. 11,246,799, which is a
(Continued)

(51) Int. Cl.
*A61H 99/00* (2006.01)
*A61N 7/00* (2006.01)
(Continued)

(52) U.S. Cl.
CPC ........... *A61H 99/00* (2013.01); *A61B 5/4519* (2013.01); *A61B 5/4848* (2013.01); *A61H 23/00* (2013.01);
(Continued)

(58) Field of Classification Search
CPC .... A61H 23/00; A61H 23/004; A61H 23/008; A61H 23/02; A61H 23/0236;
(Continued)

(56) References Cited

U.S. PATENT DOCUMENTS

| | | | |
|---|---|---|---|
| 4,364,378 A | 12/1982 | Seuss et al. | |
| 5,131,401 A | 7/1992 | Westenskow et al. | |

(Continued)

FOREIGN PATENT DOCUMENTS

| | | |
|---|---|---|
| WO | 2007005582 A1 | 1/2007 |
| WO | 2008088985 A2 | 7/2008 |

(Continued)

OTHER PUBLICATIONS

Office Action dated Sep. 16, 2016 in U.S. Appl. No. 14/219,623.
(Continued)

*Primary Examiner* — Colin W Stuart
(74) *Attorney, Agent, or Firm* — Berg Hill Greenleaf Ruscitti LLP

(57) ABSTRACT

A device and method are provided for therapy and treatment of biological tissue such as muscle, tendon, and ligament tissue, by use of a device and method in which therapeutic vibrational frequency resonance patterns are transmitted to tissues of a patient. The resonance frequencies originate from many resonance domains, including vitamins, minerals, herbs, amino acids, and fatty acids. Each domain includes therapeutic frequency resonance patterns. These resonance patterns may be passively excited and transmitted to a patient to enhance tissue function, to decrease the normal rehabilitation time of damaged tissue, and provide therapeutic benefits for muscle tissue dysfunction. Therapeutic frequency resonance patterns may also be actively excited by a delivery mechanism that uses electromagnetic or mechanical waves to interact with the device. The actively excited device transmits the therapeutic frequency resonance patterns to the patients for similar enhancements and therapeutic benefits.

21 Claims, 11 Drawing Sheets

Related U.S. Application Data continuation of application No. 14/490,378, filed on Sep. 18, 2014, now Pat. No. 10,322,063, which is a continuation-in-part of application No. 14/219,623, filed on Mar. 19, 2014, now abandoned.

(60) Provisional application No. 61/803,395, filed on Mar. 19, 2013.

(51) Int. Cl.
| | | |
|---|---|---|
| *A61B 5/00* | (2006.01) | |
| *A61H 23/00* | (2006.01) | |
| *A61H 39/00* | (2006.01) | |
| *A61H 23/02* | (2006.01) | |

(52) U.S. Cl.
CPC ............ *A61H 23/004* (2013.01); *A61H 23/02* (2013.01); *A61H 23/0236* (2013.01); *A61H 39/00* (2013.01); *A61H 39/002* (2013.01); *A61H 39/007* (2013.01); *A61N 7/00* (2013.01); *A61H 2039/005* (2013.01); *A61H 2230/60* (2013.01)

(58) Field of Classification Search
CPC .. A61H 23/0218; A61H 39/00; A61H 39/002; A61H 39/007; A61H 2039/005; A61H 99/00; A61H 2230/60; A61B 5/4519; A61B 5/4848; A61N 1/00; A61N 7/00; A61N 2/00; A61N 2/004; A61N 2/006; A61N 5/00; A61N 5/0622
See application file for complete search history.

(56) References Cited

U.S. PATENT DOCUMENTS

| | | | |
|---|---|---|---|
| 5,393,350 | A | 2/1995 | Schroeder |
| 5,597,976 | A | 1/1997 | Schroeder |
| 5,651,973 | A | 7/1997 | Moo-Young et al. |
| 5,759,198 | A | 6/1998 | Karell |
| 6,033,531 | A | 3/2000 | Brooks et al. |
| 6,132,452 | A | 10/2000 | Printer |
| 6,143,946 | A | 11/2000 | Docter |
| 6,148,822 | A | 11/2000 | Cron et al. |
| 6,424,864 | B1 | 7/2002 | Matsuura |
| 6,425,851 | B1 | 7/2002 | Kiontke |
| 6,475,514 | B1 | 11/2002 | Blitzer et al. |
| 6,558,695 | B2 | 5/2003 | Luo et al. |
| 7,035,691 | B2 | 4/2006 | Campos |
| 7,175,587 | B2 | 2/2007 | Gordon et al. |
| 8,145,318 | B2 | 3/2012 | Van Herk |
| 8,265,763 | B2 | 9/2012 | Fahey |
| 8,315,711 | B2 | 11/2012 | Campos et al. |
| 9,289,349 | B2 | 3/2016 | Doochin et al. |
| 10,322,063 | B2 | 6/2019 | Gangwish et al. |
| 11,246,799 | B2 * | 2/2022 | Gangwish ............ A61B 5/4519 |
| 2002/0031814 | A1 | 3/2002 | Brooks et al. |
| 2002/0072501 | A1 | 6/2002 | Cyr et al. |
| 2002/0156340 | A1 | 10/2002 | Blendermann |
| 2003/0118615 | A1 | 6/2003 | Blendermann |
| 2003/0181949 | A1 | 9/2003 | Whale |
| 2004/0143200 | A1 | 7/2004 | Nogami |
| 2004/0162583 | A1 | 8/2004 | Bingham et al. |
| 2006/0084891 | A1 | 4/2006 | Barthe et al. |
| 2006/0100549 | A1 | 5/2006 | Schultheiss et al. |
| 2006/0206108 | A1 | 9/2006 | Hempel |
| 2006/0239928 | A1 | 10/2006 | Heit et al. |
| 2007/0219470 | A1 | 9/2007 | Talish et al. |
| 2008/0233308 | A1 | 9/2008 | Mosaico |
| 2008/0281238 | A1 | 11/2008 | Oohashi et al. |
| 2008/0288035 | A1 | 11/2008 | Gill et al. |
| 2009/0103066 | A1 | 4/2009 | Butler et al. |
| 2009/0118816 | A1 | 5/2009 | Kipshidze et al. |
| 2009/0254008 | A1 | 10/2009 | Shields, Jr. |
| 2010/0015918 | A1 | 1/2010 | Liu et al. |
| 2011/0073462 | A1 | 3/2011 | Brooks et al. |
| 2011/0184356 | A1 | 7/2011 | Schmidt |
| 2012/0245483 | A1 | 9/2012 | Lundqvist |
| 2012/0323149 | A1 | 12/2012 | Chou |
| 2014/0200487 | A1 | 7/2014 | Ramdas et al. |
| 2014/0288471 | A1 | 9/2014 | Gangwish et al. |
| 2015/0257970 | A1 | 9/2015 | Muecke et al. |
| 2016/0015995 | A1 | 1/2016 | Leung et al. |

FOREIGN PATENT DOCUMENTS

| | | |
|---|---|---|
| WO | 2012116038 A2 | 8/2012 |
| WO | 2012160549 A2 | 11/2012 |
| WO | 2014006598 A1 | 1/2014 |

OTHER PUBLICATIONS

European Search Report dated Feb. 9, 2017 in European Application No. 15765096.1.
International Preliminary Report on Patentability dated Oct. 1, 2015 for International Application No. PCT/US2014/031221, 6 pages.
International Search Report and Written Opinion dated Dec. 18, 2015 for International Application No. PCT/US15/50695, 9 pages.
International Search Report and Written Opinion dated Jun. 25, 2015 for International Application No. PCT/US15/21554, 10 pages.
Efthimiou, et al., "Complementary and alternative medicine use in rheumatoid arthritis: proposed mechanism of action and efficacy of commonly used modalities", Rheumatol International, 2010, vol. 30, pp. 571-586.
Ke, et al., "Influence of Electromagnetic Signal of Antibiotics Excited by Low-Frequency Pulsed Electromagnetic Fields on Growth of *Escherichia coli*", Cell Biochemistry and Biophysics, 2013, vol. 67, pp. 1229-1237.
Lappin, et al., "Effects of a Pulsed Electromagnetic Therapy on Multiple Sclerosis Fatigue and Quality of Life: A Double-Blind, Placebo Controlled Trial", Alternative Therapies, 2003, vol. 9(4), pp. 38-48.
Psaltis, et al., "Holographic Memories", Scientific American, 1995, vol. 273(5), pp. 70-76.
International Search Report and Written Opinion dated Sep. 4, 2014 for International Application No. PCT/US2014/031221, 7 pages.
U.S. Appl. No. 16/395,017, filed Apr. 25, 2019.
U.S. Appl. No. 14/490,378, filed Sep. 18, 2014.
U.S. Appl. No. 14/219,623, filed Mar. 19, 2014.
U.S. Appl. No. 15/269,693, filed Sep. 19, 2016.
Serial No. PCT/US15/21554 filed Mar. 19, 2015.
Serial No. PCT/US15/50695 filed Sep. 17, 2015.

* cited by examiner

MUSCLE OPTIMIZATION DEVICE AND METHOD

CROSS REFERENCE TO RELATED APPLICATION

This application is a continuation of U.S. application Ser. No. 16/395,017, filed Apr. 25, 2019; which is a continuation of U.S. application Ser. No. 14/490,378, filed Sep. 18, 2014; which is a continuation-in-part of U.S. application Ser. No. 14/219,623, filed Mar. 19, 2014; which claims the benefit of priority under 35 U.S.C. § 119(e) to U.S. Provisional Application No. 61/803,395, filed Mar. 19, 2013, each of which are incorporated herein in their entirety by reference.

FIELD OF THE INVENTION

The present invention relates generally to the field of muscle stimulation, and more particularly, to therapy and treatment of muscle, tendon, and ligament tissue by use of a device and method in which therapeutic vibrational frequency resonance patterns are transmitted to a patient.

BACKGROUND OF THE INVENTION

Stimulation and exercise of muscle tissue is necessary for the rehabilitation and continued development of damaged and/or poorly functioning muscle tissue. The failure to stimulate and exercise muscle tissue inevitably results in muscle atrophy, and long periods of muscle inactivity can result in permanent damage.

There are a number of existing devices and methods that are used for muscle stimulation and rehabilitation, primarily in the field of neuromuscular electrical stimulation (NMES). NMES is known to provide many therapeutic benefits such as prevention or retardation of disuse atrophy, pain relief, improvement of blood circulation, and others. Most forms of electrical stimulation involve the delivery of intermittent and repeating series of electrical pulses to the targeted muscle tissue(s). In many systems, the pulses are delivered transcutaneously by surface electrodes that are placed on the patient's skin over the targeted muscle area(s).

Included within this body of knowledge regarding NMES are a number of patent references. One example includes the U.S. Pat. No. 8,265,763. This reference discloses systems and methods for neuromuscular electrical stimulation. Stimulation electrodes are provided on a stimulation pad, configured to provide electrical stimulation to a targeted tissue. A system for neuromuscular electrical stimulation also includes a pressure generating mechanism to provide a compressive force to a region of the targeted tissue, thereby removing excess fluid from the region.

Another example of a US patent reference includes the U.S. Pat. No. 8,315,711. This reference discloses a method and apparatus using resonant pulses to treat diabetes, carpal tunnel syndrome, arthritis, and other maladies by applying a stimulating signal to promote and manipulate blood flow. The stimulating signal may include a resonant sequence that includes at least three pulses, where the pulses of the resonant sequence are spaced relative to one another such that each pulse subsequent to a first pulse in the sequence is effective to progressively stimulate and create tension in a musculature that includes the muscle inwardly from the electrodes and towards the center of the musculature, while maintaining the tension created in at least a portion of the musculature by each preceding pulse in the resonant sequence.

Yet another example of a US patent reference that discloses an invention in this field is the U.S. Pat. No. 8,145,318. This reference generally discloses an apparatus for electrical stimulation of muscle tissue, including an electrode system with an electrode array. The array has a plurality of electrode pads and is placed in electrical contact with the targeted muscle tissue. The electrode system further includes a sensor for sensing a property of the muscle tissue. This property forms a measure for the activity of the muscle tissue. The apparatus includes an electrode selector for selecting one or more stimulating electrode pads. A signal generator is connected to the electrode array for providing an electrical stimulation signal to the stimulation electrode pad. A signal processor is connected to the sensor for determining from the sensor signal a value of the muscle activity, and outputting the value to a human perceptible form. This reduces the accuracy required to position the electrode system and increases the accuracy of measuring muscle tissue activity.

As further background, it is helpful to understand basic muscle physiology. When a muscle is activated during muscle testing, the muscle has "locked" because the level of neurological information flow between the muscle and the central nervous system is sufficient to maintain muscle contraction in opposition to the dynamic pressure applied. If the muscle is unable to withstand the applied pressure during muscle monitoring, the muscle "unlocks" because of insufficient neurological flow between the muscle and the central nervous system, or overt inhibition. During the muscle testing, the muscle is typically monitored in terms of the feedback to and from the muscle to check the integrity of the neurological flow between the muscle sensors (spindle cells and Golgi tendon organs) and the central nervous system. Muscle strength is defined in terms of the number and size of muscle fibers in a muscle, and the resulting force depends on alpha motor neurons, which activate the muscle fibers. Inputs from the alpha motor neurons can be excitatory or inhibitory and can come from sensory organs (e.g., the muscle spindle or Golgi Tendon Organ, or from supraspinal areas of the cerebral cortex, cerebellum, or brainstem or reflexes). Muscle strength can be measured by the weight that can be lifted by that muscle or force that can be exerted by the muscle (e.g. as measured on a dynamometer). A "strong" muscle is one that when "locked" can hold against a large weight, while a "weaker" muscle is "over powered" by the same weight even when all muscle fibers are "locked". Thus, the "weaker" muscle can still "lock", that is, maintain sufficient neurological flow to hold against all pressures up to that which over powers it. An "unlocked" muscle, however, cannot maintain sufficient neurological flow to hold its position even at pressures far below that which are needed to overpower it. When the muscle is inhibited, too few muscle fibers can contract to equal the pressure applied and thus the appendage containing the muscle being tested will begin to move in the direction of pressure. This failure of the muscle is not caused by the muscle being "weak" but rather, is caused by the muscle experiencing poor functioning by problems associated with the inputs to the muscle from some other part of the nervous system.

All muscles in the body with few exceptions (the diaphragm being one) are arranged in antagonistic pairs of muscles. This arrangement of muscles can be referred to as reciprocal facilitation/inhibition, because whenever one of the pair is facilitated or turned on, its antagonist (or antagonists as there may be several) is automatically inhibited or turned off. Hence, the turning on or "locking" and turning off or "unlocking" are both normal states of muscle function. When a muscle "locks" during muscle monitoring, neurologically, signals are sent to the "prime mover" (PM) to hold the position of the body part by consciously facilitating (turning on) the PM. Then as the pressure on the body part (e.g. an arm held horizontal) is increased during muscle monitoring the muscle sensors (spindle cells) in the PM respond by a spinal reflex arc referred to as the "load reflex". The load reflex increases the degree of PM contraction, while at the same time inhibiting their antagonists and facilitating their synergists. Synergists are muscles that help the PM in holding the arm up, but are not in their position of optimal mechanical advantage. Synergists contribute much less than the PM to establishing and maintaining this position. A muscle circuit can be defined as the PM and all other muscles, both synergists and antagonists, to which it is "wired" both at the level of the brain and spinal reflex arcs.

FIG. 1 provides an example of a simplified muscle circuit. More specifically with respect to a muscle circuit, each muscle in the body has antagonists (usually more than one) that oppose its action. The agonist or PM and its antagonist(s) are neurologically wired together via the spindle cells in the belly of these muscles. This neurological wiring is such that when a PM is facilitated (turned on) it sends signals to automatically inhibit (turn off) its antagonist(s) to the same degree it has been facilitated. At the same time, if the load is sufficiently large it facilitates its synergists. In this way, the limb moves in the direction of contraction, unopposed by its antagonist(s), permitting smooth and rapid movement of the limb. Likewise, facilitation of an antagonist will inhibit the PM, as the spindle cells of the antagonist(s) need to inhibit the PM in order to move the limb in the opposite direction from the action of the PM. Referring to FIG. 1, it illustrates a muscle circuit consisting of an agonist or prime mover (biceps), one antagonist (triceps) and one synergist (brachioradialis). The spindle cell of the PM is wired to both its antagonist, which it inhibits, and its synergist, which it facilitates. Not shown is the reciprocal spindle cell circuitry for the antagonist, the triceps. When the triceps is facilitated, spindle cells in the belly of the triceps send signals to inhibit the biceps and its synergists the brachioradialis.

During a series of muscle contractions and relaxations, information on this series of activity is also sent to subconscious parts of the brain, e.g. the basal ganglia and thalamus which control "pre-recorded" muscle programs, and the cerebellum where comparisons are made of intended actions and actual actions. If an intended action is to keep the arm held at horizontal, but the arm moves downward due to the increasing pressure of a dynamic load, the subconscious brain centers augment the automatic spinal load reflex and orders additional contraction of the PM to offset movement, thereby helping the arm to remain horizontal. As long as the flow of information from muscle sensors to and from the brain remains "clear" with no interruptions, the muscle can "lock" and maintain its "lock" under continued loading until the muscle reaches its full power of contraction. If loading continues above this point, the arm will move down as the PM is overpowered by the downward pressure of the dynamic load.

During muscle testing, the pressure applied is far less force than needed to overpower the PM. A muscle with full neurological integrity should therefore "lock" during muscle monitoring. That is, unless something interferes with the neurological flow of information between the muscle and the central nervous system, the muscle should be facilitated sufficiently to maintain its physical position even under increasing load. This capability of the muscle to "lock" indicates a muscle that can be considered in "balance" with its neurological circuitry. If there is interference or a disruption in the flow of information between a muscle and the central nervous system, the muscle will not be able to coordinate and match its degree of facilitation to the increasing loading taking place during muscle testing/monitoring. Accordingly, the arm will move downward appearing to fail under the monitoring pressure, resulting in the "unlocked" muscle state. A muscle that becomes unlocked such as by inhibited feedback from muscle spindle cells, tendon and joint sensors or inhibitory feedback from subconscious emotional brain centers, can be described as being "under-facilitated" relative to the pressure being applied. This unlocking of the muscle may be observed simply as the muscle being weak (i.e. failing under the monitoring pressure). However, the muscle is not weak, but rather inhibited or under-facilitated to resist the monitoring pressure.

As additional background, muscle function is controlled by a number of different sensors in the muscles themselves, their tendons and the ligaments of the joints among others. Together these sensors that sense position, length, and tension of muscles are called "proprioceptors". There are several types of proprioceptors that provide the central nervous system (CNS) with feedback with regard to what is happening in the muscles, body position and equilibrium. The feedback from these sensors, which are actually specialized nerve endings, goes entirely to the spinal column and subconscious parts of the brain, e.g. spinal segments, brainstem, basal ganglia, thalamus, cerebellum, etc. This provides the body with information on the state of muscle contraction, muscle and tendon tension, position and activity of joints and equilibrium. When stimulated, many of these proprioceptors adapt quickly and provide information on instantaneous change and rate of change in muscle activity and body position. Others adapt only slowly to stimulation and therefore provide steady-state information about muscle and body position. Working together they provide the information necessary for coordinated muscle action and movement and the maintenance of posture.

For muscle to function properly, they require a number of different nutrients, including vitamins, minerals, and trace elements in sufficient concentrations to maintain the required energy production for muscle function. Muscle tissue also requires a variety of amino acids for structural integrity and repair, and to provide energy for proper muscle function. When any of the components of this nutritional matrix is deficient, it may reduce the effectiveness of muscle function. Additionally, the proper ratios and concentrations of the nutrients within this matrix are necessary for maintenance of on-going muscle function. One of the problems of aging is a decrease in the effectiveness with which the body both assimilates and utilizes nutrients and thus muscle function is often affected by these nutrient imbalances due to these natural processes.

While there may be a tremendous amount of information available regarding traditional techniques and therapies for improving muscle function, the great majority of this information relates to electrical or chemical methods of treatment. Muscle stimulation by NMES has proven to provide certain benefits. Providing a patient with an improved diet and/or supplementation of vitamins, minerals, and other nutrients that were shown to be lacking has also proven to provide certain benefits.

However, nutritional supplementation, stimulation and exercise alone are often not enough to strengthen "weak" muscles due to inhibition of the muscle via muscle spindle cell, Golgi tendon organ and Golgi ligament organ receptors whose job it is to "protect" the structural integrity of the muscle and its related tendons and ligaments should tension on the muscle exceed a threshold level. Often injury or even simply slipping or an unusual activity can "unset" this threshold for inhibition such that the Spindle cell, Golgi tendon organ or Golgi ligament organ receptors now inhibit the muscle action long before there is any likelihood of damage to the muscle, tendon or ligament. Thus, when the person now tries to use this muscle it appears "weak" as it just cannot develop much power.

A muscle in this "inhibited" state responds very poorly to normal rehabilitation even using the electrical stimulating devices because according to Wolf's Law in physiology, in order to build more strength, and muscle must develop more tension. This is because tension is the signal for the muscle to make more muscle fibers, which is what increases its strength. If, however, the muscle is inhibited at a specific level of tension (even one that does not approach tension that would be harmful) by the "unset" Spindle cell, Golgi tendon or Golgi ligament organ receptors, this inhibition prevents the development of further tension, and thus the muscle is not given the signal to make more muscle fibers. Muscles inhibited in this way, even when exercised regularly can never get stronger, and thus present as chronic muscle problems. Until the "unset" receptors are "reset", this problem will persist.

Thus, traditional techniques and therapies for improving muscle function still may not provide optimal results for many patients that have certain imbalances or maladies manifesting in poor muscle function. Therefore, there is still a need to provide an alternative form of treatment and therapy for muscle tissue that does not rely upon traditional techniques/therapies.

SUMMARY OF THE INVENTION

In accordance with the present invention, a device and method are provided for therapy and treatment of biological tissue such as muscle, tendon, and ligament tissue, by use of a device and method in which therapeutic vibrational frequency resonance patterns are transmitted to muscle and muscle proprioceptors of a patient. Disease states that may be treated or ameliorated using the devices and methods of the present invention include multiple sclerosis, Parkinson's disease, cerebral palsy, amyotrophic lateral sclerosis (Lou Gehrig's Disease ALS), muscular dystrophy, and Graves' disease, spinal-bulbar muscular atrophy, myasthenia gravis, Huntington's Disease, polymyositis, Lambert-Eaton syndrome, monomelic amyotrophy, progressive bulbar palsy, lower motor neuron weakness, upper motor neuron weakness, peripheral neuropathy, diabetic peripheral neuropathy, spinal cord injuries, botulism, Guillain Barre syndrome, and Pompe disease. Devices and methods of the present invention may also be used in coordination with rehabilitation, physical therapy, and sports training.

According to the present invention, it may be considered a device and method in which therapeutic resonance frequencies are transmitted to, or interact with, a patient, in which the resonance frequencies originate from many resonance domains, including vitamins, minerals, herbs, amino acids, and fatty acids. The particular combination of the domains used in the present invention may be referred to as a "muscle formula", as explained further below. Each of the domains includes respective therapeutic frequency resonance patterns. These resonance patterns are identified, captured, and ultimately delivered to a mineral matrix component of the device. The combined resonance patterns are "embedded" in the mineral matrix. The mineral matrix includes minerals/elements including, but not limited to, calcium, potassium, magnesium, silica, boron, carbon, and nitrogen. The mineral matrix is applied to a reverse side of a carrier or substrate layer, such as a small piece of silicone, glass, or a thermoplastic material. The mineral matrix is capable of retaining the combined or master frequency resonance patterns for a period of time. The resonance frequencies retained by the mineral matrix can be transmitted to a patient to enhance muscle, tendon, and ligament function, to decrease the normal rehabilitation time of a damaged muscle/tendon/ligament, and may otherwise provide therapeutic benefits for muscle tissue dysfunction.

As best understood at the present time, these therapeutic frequency resonance patterns generally relate to the nuclear magnetic resonance characteristics of each of the chemical compounds of the resonance domains. In a simplified summary, it is known that all molecules residing at a temperature above absolute zero will exhibit vibrational characteristics due to thermal agitation or thermal noise. When charged groups of atoms on a molecule vibrate, electromagnetic fields are created in the surrounding space. Therefore, molecules in this explanation can be viewed as oscillators. The particular frequencies at which atoms or molecules oscillate/radiate are known. Astronomers are capable of determining the chemical makeup of distant stars, and analytical chemists can identify specific inorganic and organic molecules, and/or determine the atomic structure and composition of a molecule by recording the corresponding emission or absorption spectra. Tissue can also be viewed as having its own primary resonance frequency based upon the particular dominant chemical compounds/molecules which make up the tissue being treated.

It has been theorized that the human body responds directly to the frequencies or molecular resonance of substances including but not limited to, nutrients, hormones, neurotransmitters, neuropeptides, and cytokines. This response by the body is not reliant upon actual contact of the substances with the body. Like the tuning-fork effect, a first tuning fork vibrating at its resonance frequency will cause another tuning fork of the same frequency to begin to vibrate at the same frequency, even though the other tuning fork does not contact the first tuning fork and is located apart from the first tuning fork. Via the same phenomenon, molecular resonance transfers vibrational frequencies between similar molecules or similar parts so that the physically remote molecules will resonate with each other, even when they are not touching. In this way, therapeutic response frequency resonance patterns may generally mimic electromagnetic signals of nutraceuticals and other bodily components. The manner in which frequencies interact with nutrients and other molecules within the body is a topic of current research. It has been proposed that molecular resonance actually results from quantum resonance.

A recent study conducted in the United Kingdom involved research on how molecules interact via their emitted or radiated frequencies. This study evolved from successful treatments of people with electromagnetic sensitivity. In the study, clinical data supported a conclusion that a chemical in a sealed vial or ampoule can trigger an allergic reaction, for example, without the substance being introduced into the patient's body or touching their body. Thus, a reasonable mechanism to explain these phenomena is that the molecules in the sealed vial when placed near the body transmit their specific frequencies to the body via the weak electromagnetic fields that they emit, which in turn interacts with the resonance frequencies of molecules within the body. These resonance frequencies can interact in two ways according to physics: 1) by constructive interference, which will enhance the coherence of the two interacting frequencies with the more coherent field entraining the less coherent field into greater harmonic resonance; or 2) by destructive interference which will reduce the coherence of the two interacting fields reducing the harmonic resonance of the two fields. In the case of allergic substances in the sealed vials, the resonance frequencies emitted interacted with destructive interference with the molecules in the body triggering an allergic reaction.

In summary, it is the frequencies radiated by the molecules and not the chemicals themselves that disrupt regulatory systems (destructive interference), or that restores these systems to normal operation (constructive interference). These phenomena fall into the category of external or exogenous homeopathy in which the remedy does not touch the body, yet produce a specific physiological effect, e.g. an allergic reaction, or the elimination of an allergic reaction. This provides a model for how the frequency resonance patterns of the nutrients in the muscle formula may be transmitted in the form of molecular resonance via quantum coherence to the tissues of the muscles, tendon and ligaments, and that this molecular/quantum coherence entrains the aberrant frequencies that have caused the muscle dysfunctions bringing the muscle back into homeostatic function, even when the device of the present invention is not physically touching the body or placed directly on the muscle being treated.

One preferred embodiment of the device of the present invention includes a relatively small carrier or substrate layer, and a coating applied to one side of the substrate containing the mineral matrix. One convenient sized carrier or substrate that can be used is a standard computer/information chip, similar to chips that may be used as electronic sales tags that are programmed with basic information such as the cost of an item, manufacturer, inventory data, etc. A computer chip can be used as a convenient substrate for a number of reasons. First, these chips are mass produced, and are relatively inexpensive. Secondly, these chips are relatively small, yet are of a size that provides adequate surface area for applying the mineral matrix. Thirdly, the chips are structurally robust and are made of materials that readily accept and hold an applied coating. While a computer chip provides a good solution as a carrier/substrate layer, it should be understood that other materials could be used.

In another aspect of the invention, use of a computer chip also allows the device of the invention to have the capability of being electronically "tagged" in order to provide product identification, inventory control, and other inventory or sales functions. Therefore, the computer chip could be programmed/encoded with the desired information in order to provide the desired inventory or sales function.

The coating is applied to the side of the chip that does not contain the circuitry, and in the case of using a holographic chip, the coating is applied to the side of the chip that does not contain the hologram. The coating includes a liquid or slurry containing the mineral matrix. As mentioned, the mineral matrix may include, but is not limited to, sodium, magnesium, calcium, boron, and silica, and combinations thereof. The mineral matrix is mixed with an adhesive glue. The coating containing the mineral matrix is applied at a thickness of approximately 0.25 mm. The mineral matrix makes up approximately 50% by weight of the mineral matrix/glue mixture. When completed, the chip according to this preferred embodiment is approximately 26 mm×22 mm in length/width, and 0.5 mm thick.

Also in accordance with the preferred embodiment, the resonance frequencies of the muscle formula must be embedded within the mineral matrix. First, the muscle formula is prepared by grinding and mixing the constituent components of the formula. Listed below are chemicals/compounds/plant types that may be used within the muscle formula. These chemicals/compounds/plant types may be used in different quantities/concentrations within the muscle formula to achieve specific objectives for the treatment to be conducted. Although a specific listing of components is provided, it should be understood that the muscle formula can incorporate a host of other components, and therefore this listing should not be considered as exclusive. These components may include:

L-Phenylalanine
L-Glutamine
L-Carnitine
L-taurine
Betatene
Lemon bioflavonoids
Lithium
Thiamine (Vitamin B1)
Riboflavin (Vitamin B2)
Nicotinamide (Vitamin B3)
Calcium pantothenate (Vitamin B5)
Pyridoxine (Vitamin B6)
Methylcobalamin (Vitamin B12)
Folic acid
Biotin
Ascorbic acid (Vitamin C)
Rosehips
Vitamin D
Vitamin E (preferably, d-alpha)
Inositol
Choline
Lecithin
Calcium gluconate
Magnesium stearate
Silica
Iron gluconate
Zinc gluconate
Manganese gluconate
Chromium sulphate
Potassium iodide
Minerals
D-Ribose
Hyaluronic acid
Chondroitin sulphate
Glycosylated glucosamine
Collagen
Creatine monohydrate,
Kelp
Alfalfa, and combinations of these components.

The lithium may include organic sources of lithium, such as lithium found in brewer's yeast (*Saccharomyces cerevisiae*).

The D vitamin may be supplied as vitamin D3 (cholecalciferol) and/or vitamin D2 (ergocalciferol).

The minerals may include any elements selected from: Ag, Al, As, Au, B, Ba, Be, Bi, Br, C, Ca, Cd, Ce, Cl, Co, Cr, Cs, Dy, Er, Eu, F, Fe, Ga, Gd, Ge, H, Hf, Hg, Ho, I, In, Ir, K, La, Li, Lu, Mg, Mn, Mo, N, Na, Nb, Nd, Ni, O, Os, P, Pb, Pd, Pr, Pt, Re, Rh, Ru, S, Sb, Sc, Se, Si, Sm, Sn, Sr, Ta, Tb, Te, Th, Ti, Tl, Tm, V, W, Y, Yb, Zn, and Zr. Preferably, these minerals are used or added to other components of the muscle formula as a colloidal suspension.

Lemon bioflavonoids are anthoxanthins (flavones and flavonols) that may include isoflavonoids derived from 3-phenylchromen-4-one (3-phenyl-1,4-benzopyrone) and neoflavonoids, derived from 4-phenylcoumarine (4-phenyl-1,2-benzopyrone).

The collagen proteins may be type I or type II, or a combination thereof.

Alfalfa, also called lucerne, may include flowering plants in the pea family Fabaceae.

Kelps include any genera of brown algae, Phaeophyceae, in the order Laminariales.

After being mixed, the components are dissolved in an aqueous solution an alcohol, preferably ethanol. A sample of the aqueous alcohol solution is placed into a first quartz chamber (the "master crystal"). The first quartz chamber containing the solution is then placed into an apparatus having a ruby laser located above the first quartz chamber. The first quartz chamber may be, for example, a chamber that holds a 5 ml amount of the muscle formula solution. A second quartz chamber is provided, and has therein a buffered salt solution comprising selected salts, comprising, but not limited to, sodium, magnesium, calcium, chloride, nitrates, silica, or bicarbonates, or combinations thereof. This second quartz chamber also includes a quartz crystal placed in the quartz chamber. The second quartz chamber is provided directly below the first quartz chamber. The laser is activated, and the laser results in excitation of the components of the muscle formula solution so that the frequency resonance characteristics of the muscle formula solution are transferred to the quartz crystal in the second chamber. The transferred frequency resonance characteristics are retained in the quartz crystal in the form of a combined frequency resonance pattern transferred to the quartz crystal. The buffered salt solution stabilizes this frequency resonance pattern transferred to the quartz crystal. Accordingly, this process transfers into the quartz crystal/salt solution the combined frequency resonance pattern of each component of the muscle formula into a single frequency resonance matrix of the whole muscle formula (MF), hereinafter referred to as the MF frequency resonance matrix. This quartz crystal-salt solution programmed with the MF frequency resonance matrix is referred to as the master crystal, and it has been shown to maintain this frequency resonance matrix over time.

Thus, another embodiment of the invention is a composition comprising at least two components making up the muscle formula, including L-phenylalanine, L-glutamine, L-carnitine, L-taurine, betatene, lemon bioflavonoids, lithium, thiamine (vitamin B1), riboflavin (vitamin B2), nicotinamide (vitamin B3), calcium pantothenate (vitamin B5), pyridoxine (vitamin B6), methylcobalamin (vitamin B12), folic acid, biotin, ascorbic acid (vitamin C), rosehips, vitamin D, vitamin E (preferably, d-alpha), inositol, choline, lecithin, calcium gluconate, magnesium stearate, silica, iron gluconate, zinc gluconate, manganese gluconate, chromium sulphate, potassium iodide, minerals, D-ribose, hyaluronic acid, chondroitin sulphate, glycosylated glucosamine, collagen, creatine monohydrate, kelp, alfalfa and combinations of these components. These compositions may be dissolved or suspended in an alcohol, such as an aqueous alcohol solution. In certain embodiments, the alcohol of these compositions is ethanol.

In order to transfer the MF frequency resonance matrix to a the device of the present invention, the ruby laser is arranged to send a pulse of light directed to shine through the master crystal onto each individual computer chip of a roll of coated computer chips that will move past the tip of the master crystal at a specific speed. When the laser is turned on, as each computer chip passes the tip of the master crystal, the pulse of laser light transfers the resonance MF frequency matrix into the mineral matrix previously coated onto the chip. A thin plastic film is then coated on the mineral matrix layer to provide additional protection. The mineral matrix retains the resonance MF frequency matrix, and therefore can later serve as a "transmitter" of the retained frequencies during use of the device.

According to the method of the present invention, the frequency resonance matrix of the muscle formula can be delivered to the body in many ways. According to a first method, the muscle chip device may be applied directly to the body for a period of time, while the person performs certain activities that activate specific muscles involved in different patterns of motor activity, thereby re-integrating muscle dysfunction. According to this method, the device may be applied directly over the targeted group of muscles to be treated, and then directed exercises are performed to achieve the therapeutic effect. For example, this direct application method can be achieved by placing the chip on the skin over the affected muscle (such as a bicep muscle), and then the bicep muscle is taken through a series of contractions for a period of 5 to 18 seconds.

According to another method of the invention, the frequency resonance matrix of the muscle formula can be delivered to the body by placing the device on the acupoint central vessel 8 (the navel), which is considered in Traditional Chinese Medicine the most receptive acupoint on the body. The targeted muscle(s) are then directed to be held in their most contracted position for approximately 5 seconds while a load is applied to the body part that is supported by the targeted muscle(s). The targeted muscle(s) are then relaxed for a period of approximately 30 seconds, and the targeted muscle(s) is then directed to be locked for approximately another 5 seconds, while increasing pressure is applied against the locked muscle. Through Electromyographic (EMG) testing (described below), it has been shown that this method can reset muscle proprioception. After a period of approximately 2 minutes, the integrity of muscle function can be re-checked to confirm that the muscle proprioception has been reset. If successful, the targeted muscle(s) should now lock strongly against monitoring pressure, yet should be able to be sedated using spindle cell, golgi tendon organ and golgi ligament organs sedation techniques.

The frequency resonance matrix of the muscle formula may also be actively excited. In the embodiments described above, the muscle chip or device is passively excited by the manipulation of the targeted muscle(s). In other embodiments, a delivery mechanism is configured to actively excite the muscle chip or device such that the muscle chip or device produces the frequency resonance matrix of the muscle formula. Similar to the passive systems, the active excitation of the muscle chip or device is used to deliver a therapeutic benefit to a patient.

According to the theory supporting the therapeutic benefits of the present invention, muscle imbalance or dysfunction can be caused by the lack of or incoherence of certain frequencies needed to maintain homeostatic function. Direct activation or dynamic muscle activity activates the frequencies causing the muscle imbalance. This 'activation field' created by activation of the muscle imbalance via resonance is entrained by the more coherent frequencies imbedded in the mineral matrix of the device of the present invention, and the device generates a harmonic resonance field to replace or supplement the 'missing' or 'distorted' frequencies involved in the muscle imbalance. Thus, the affected muscle can be brought back into homeostatic function by transferring the harmonic resonance fields retained in the mineral matrix of the device to the muscle, thereby resetting muscle function.

Treatment by use of the invention can be enhanced if the caregiver has a working knowledge of muscle function, including how to position muscles for proper muscle monitoring. Treatment can be further enhanced if the caregiver has a working knowledge of muscle monitoring or muscle testing techniques to include knowledge in the use of an indicator muscle. An indicator muscle is a muscle in proprioceptive homeostasis that can be used to locate a frequency match between the frequency resonance pattern of a specific muscle dysfunction and these same frequency resonance patterns of one or more of the components in the device. Treatment can be further enhanced by knowledge of acupressure as it relates to the application of relevant acupressure therapy in Traditional Chinese Medicine and Ayruvedic Medicine models.

The device and method of the present invention can rapidly reset muscle proprioception to restore normal muscle function, often resolving even long-term chronic pain and dysfunction. The device and method may further reduce days of stay in a hospital, reduce rehabilitation times, reduce need for many operations, and save the hospital and insurance systems time and resources, as well as to save patients out of pocket costs. This invention is also non-invasive with only minimal side-effects ever recorded. Through IRB-approved university research, it has been found that muscle improvement can take place, often within seconds, and these benefits appear to be long-lasting.

In embodiments of the present invention, the resonance frequency of a particular layer may depend on its physical attributes. For example, the size of the layer influences the resonance frequency. In crystals such as quartz, how the crystal is cut influences the resonance frequency. In an "AT" type of crystal cut, the crystal's x axis is inclined by approximately 350 relative to the z axis. This cut results in a crystal that is less sensitive to fluctuations in temperature. Additionally, the material that the layer is comprised from influences the possible resonance frequency.

In some embodiments, a delivery mechanism is used to excite the device layers to produce the resonance frequency and/or harmonics thereof. Delivery mechanisms generally produce two types of waves to excite the device: electromagnetic waves and mechanical waves such as acoustic waves. These waves interact with attributes of the device such that the device produces the resonance frequency. For example, in some embodiments the device is a piezoelectric crystal and the delivery mechanism imposes an electric field on the crystal which causes the crystal to change shape. When the delivery mechanism ceases to impose an electric field, the crystal reverts back to its original size and shape, and the crystal emits a resonance frequency. This resonance frequency and harmonics thereof may then be implemented to a user for therapeutic benefit.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
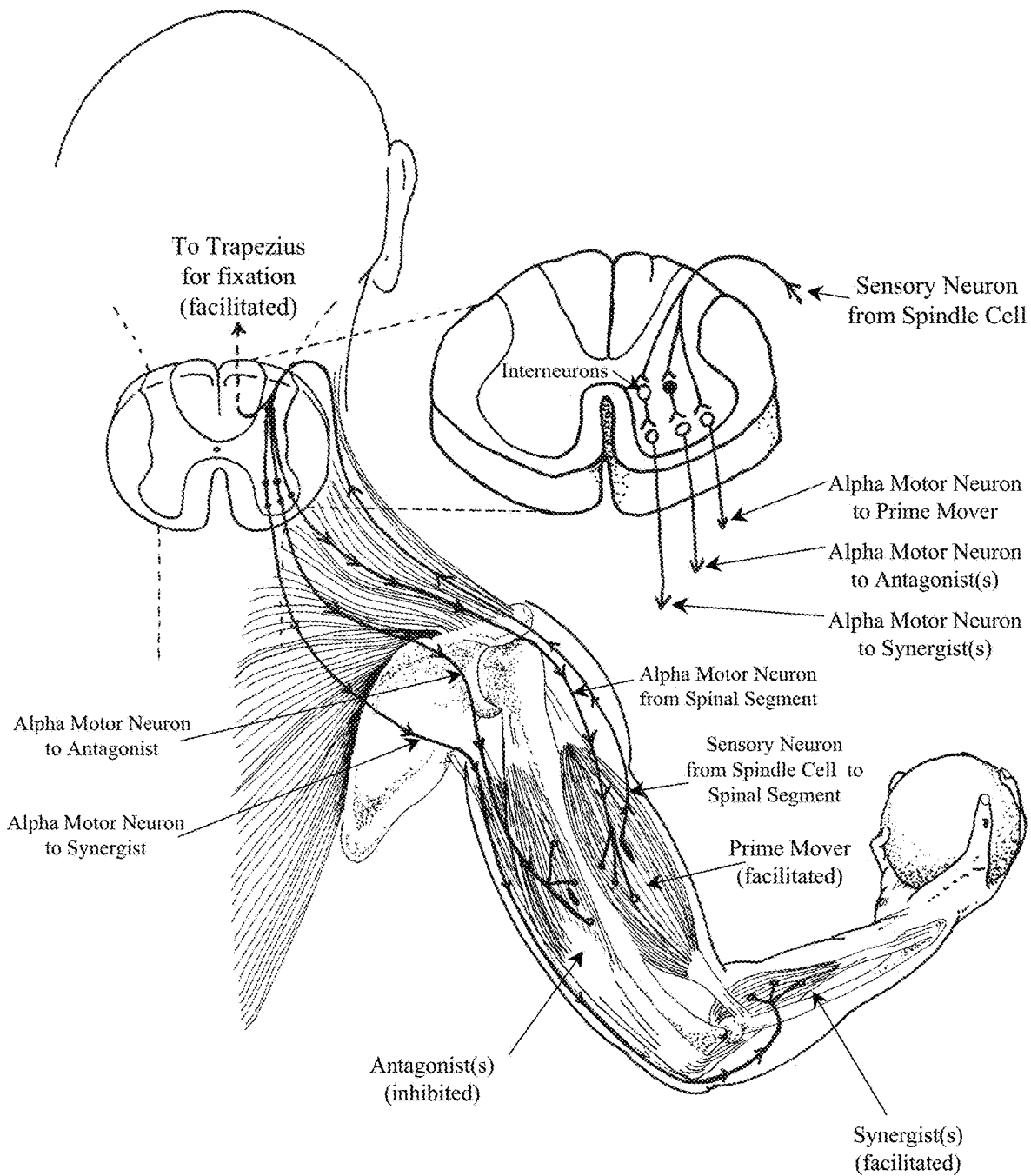
FIG. 1 is a simplified schematic diagram of muscle circuit as mentioned above.
Figure 2:
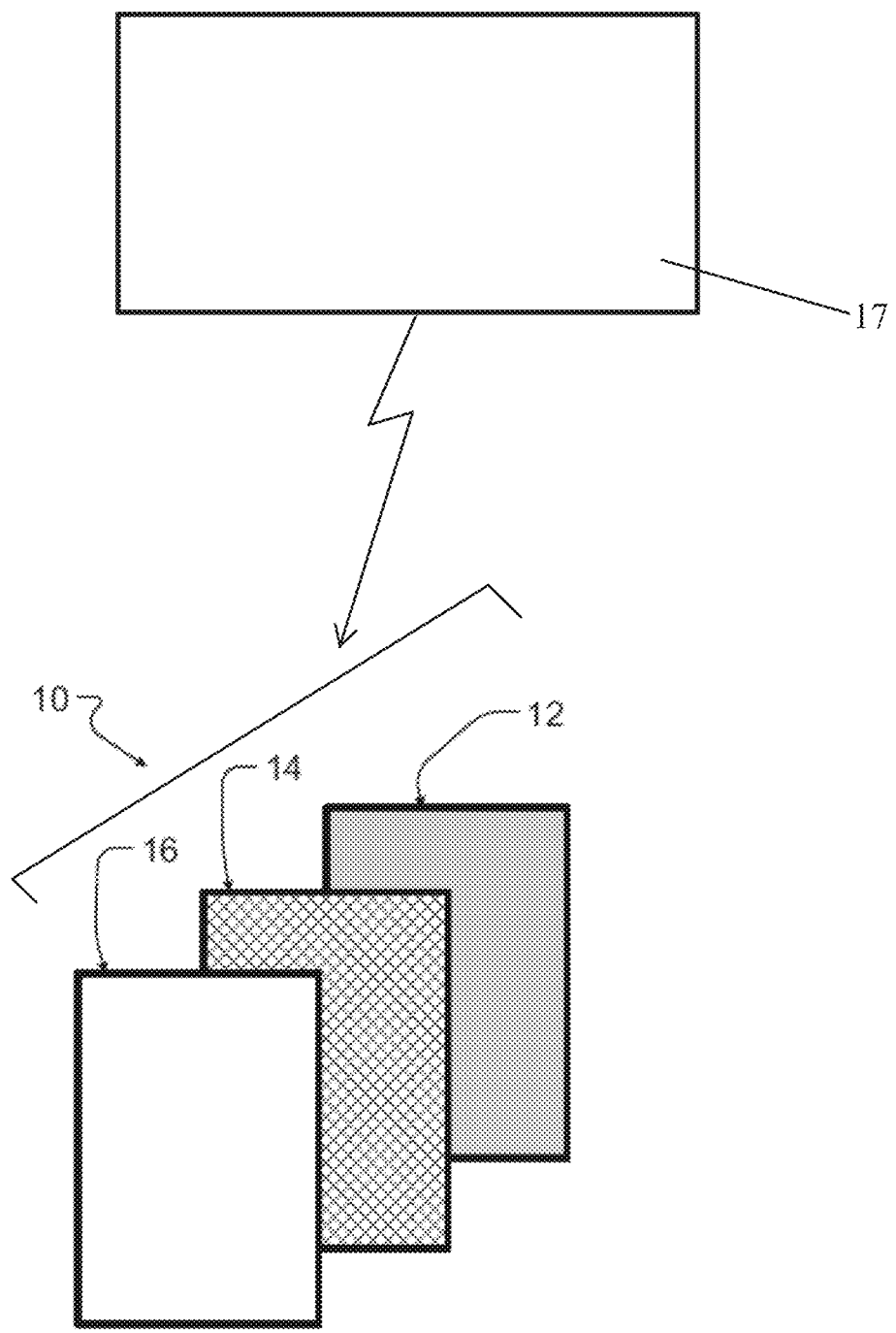
FIG. 2 is an exploded perspective view of the device of the present invention in a preferred embodiment.

Referring to FIG. 2, a preferred embodiment of the device 10 of the present invention is shown in an exploded perspective view. In one aspect, the device can be generally referred to as a therapeutic frequency resonance pattern delivery device or means. This figure illustrates the device 10, having a substrate or carrier layer 12, a mineral matrix layer 14, and a protective layer 16. In other embodiments, a delivery mechanism 17 may be used to actively excite a frequency response from the device 10. As described, the substrate or carrier layer 12 may be a computer chip. The mineral matrix layer 14 is applied to one side of the carrier layer 12, and is mixed with adhesive glue. The mineral matrix layer 14 is applied at a thickness of approximately 0.25 mm. The mineral matrix makes up approximately 50% by weight of the mineral matrix/glue mixture. When completed, the device 10 according to this preferred embodiment is approximately 26 mm×22 mm in length/width, and 0.5 mm thick. Optionally, the carrier layer 12, if a computer/holographic chip are used, may further include information programmed/recorded on the chip for sales and inventory purchases, or to otherwise identify the chip. The protective layer 16 may be a thin plastic film applied over the mineral matrix layer 14 to provide protection for the layer 14. This thin plastic film will not degrade or otherwise hinder the transmission capability of the mineral matrix layer 14. The device 10, which utilizes a computer chip as the substrate, is shown as having a rectangular shape. However, which also be understood that the device 10 can be other shapes, such as round, oval, or any other shape which makes use of the device convenient when attached to a patient.

Figure 3:
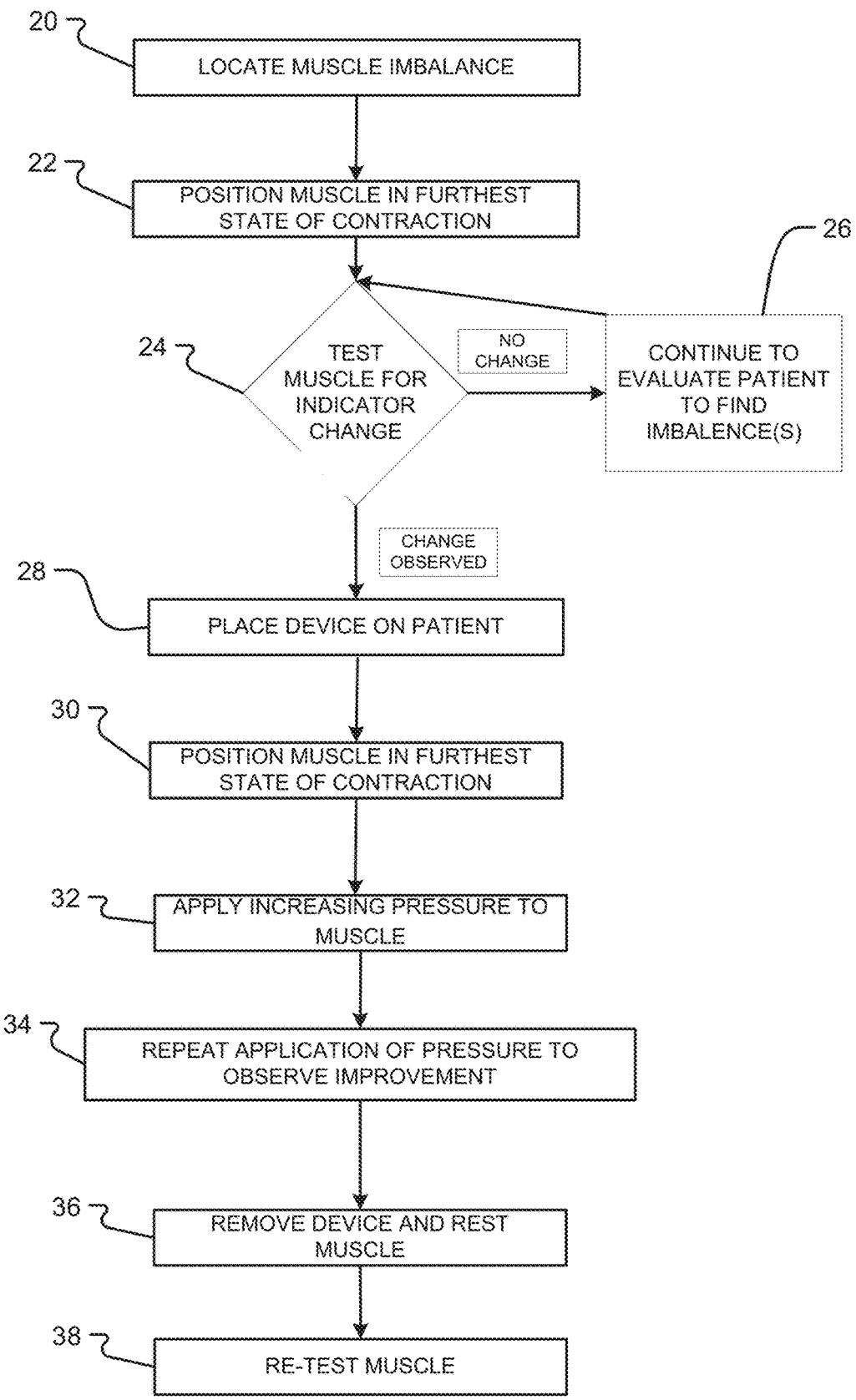
FIG. 3 is a simplified flow diagram of the method of the present invention in a first embodiment of the method.

Referring to FIG. 3, a simplified flow diagram is provided for explanation of one preferred embodiment of the method of the invention. At block 20, as a first step, a caregiver locates a muscle imbalance. At block 22, the affected body part is positioned so that the targeted muscle is in the furthest state of contraction. This contracted position is held for approximately 5 seconds. At block 24, the muscle is tested for an indicator change by applying a steady, consistent pressure. If there is no indicator change, that is, if there is no observed, "unlocking" or failure of the muscle, then at block 26, the patient continues to be checked/evaluated for other muscle imbalances. If there is an observed, "unlocking", then at block 28, the device 10 is placed on the central vessel (the navel). At block 30, the targeted/imbalanced muscle is again placed in its furthest state of contraction. At step 32, increasing pressure is applied for approximately 5 seconds to activate the muscle fibers, and the associated spindle cells, golgi tendon organs and golgi ligament organs. This activity of block 32 is repeated a number of times, shown at block 34. During this repeated application of pressure over 5 second time periods, the caregiver should observe improved muscle function. In clinical trials, it is been shown that repeating this activity three or four times has been adequate to resolve many muscle imbalance problems. At step 36, the device 10 is removed from the patient, and the muscle is allowed to rest for a period of time, preferably for about 2 minutes. At step 38, the muscle is retested by placing the muscle back to its furthest state of contraction. If the procedure has been successful, the targeted muscle(s) should now lock strongly against monitoring pressure.

Figure 4:
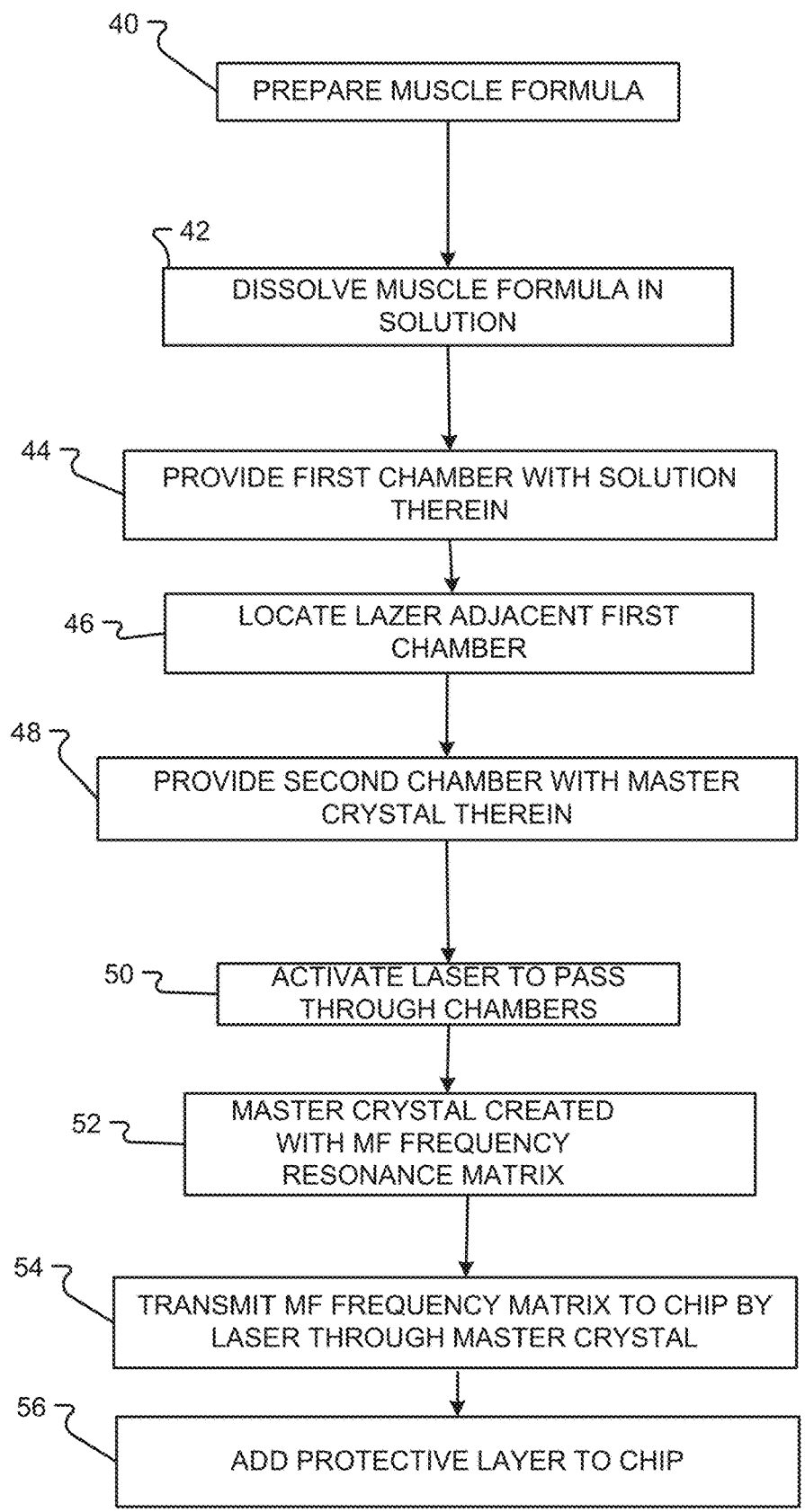
FIG. 4 is a simplified flow diagram of a method of manufacture for the device of the present invention.

The method described in reference to FIG. 3 prescribes placement of the device 10 on the navel; however, it should be understood that the device 10 can be placed upon other body parts, to specifically include those muscles that have been found to have an imbalance. Additionally, although the method described prescribes application of repeated and progressively increasing pressure over 5 second time periods, other methods of the present invention may include other protocols for application of pressure over other time periods, as well as the number of cycles in which pressure is applied. For example, for some muscle groups, it may be found that applying pressure over lesser or greater time periods may be preferred. As best understood, the resonance frequencies are transmitted to the patient passively. For instance, the movement of the individual muscle or muscle group excites a frequency response from the carrier layer 12 and/or mineral matrix layer 14 of the device 10. As mentioned, a delivery mechanism 17 may be used to actively excite a frequency response from the device 10. Referring to FIG. 4, a simplified flow diagram is provided for the basic steps in manufacturing the device 10. As shown, block 40 is the preparation of the muscle formula in which the formula is prepared by grinding and mixing the constituent components of the formula. At block 42, after the components have been mixed, the components are dissolved in an aqueous solution of alcohol. At step 44, a first quartz chamber is provided that contains the aqueous solution. At step 46, a ruby laser source is located adjacent the first quartz chamber. At step 48, a second quartz chamber is provided, and the second quartz chamber contains a buffered salt solution comprising selected salts, and a quartz crystal. The second quartz chamber is positioned on the opposite side of the first quartz chamber as compared to the position of the ruby laser source. At block 50, the laser is activated, and the laser beam first passes through the first quartz chamber into the second quartz chamber. The passing beam of the laser through the first quartz chamber results in excitation of the aqueous solution so that the frequency resonance characteristics of the muscle formula are transferred to the quartz crystal in the second quartz chamber. The transferred frequency resonance characteristics are retained in the quartz crystal in the form of a combined frequency resonance pattern transferred to the quartz crystal. The buffered salt solution stabilizes this frequency resonance pattern transferred to the quartz crystal. This method transfers into the quartz crystal/salt solution the combined frequency resonance pattern of each component of the muscle formula into a single frequency resonance matrix, the MF frequency resonance matrix. Thus, the quartz crystal-salt solution "programmed" with the MF frequency resonance matrix is the master crystal, and the master crystal has been shown to maintain this frequency resonance matrix over time. Block 52 signifies that the master crystal has been created with the embedded MF frequency resonance matrix, and then can be used in production for transferring the MF frequency resonance matrix to the individual chips/devices 10. At block 54, the ruby laser is arranged to transmit a pulse of light directed to pass through the master crystal onto each individual chip as they pass the tip of the master crystal at a controlled speed. Many types of computer/holographic chips are provided in rolls with individual chips being spaced from one another along the length of the roll. Therefore, the ruby laser can be programmed to transmit its laser beam on each individual chip as it passes the location of the master crystal. At block 56, after each chip/device 10 has received the MF frequency resonance matrix, each chip then receives its corresponding transparent protective layer 16.

Data has been collected in a proof-of-concept study and an IRB-approved university trial assessing muscle function using the device and method of the invention. In initial clinical studies the invention has been shown to reliably produce consistent improvements in muscle function. One common measure of muscle function is termed Electromyography or EMG that measures the electrical activity of the individual motor units as they shorten during contraction. In EMG, the Electromyograph is attached to a recording electrode which is either a needle inserted into the muscle to record muscle activity, or to a transcutaneous electrode that records electrical activity of the muscle from the surface of the skin. In the university study, transcutaneous electrodes were used. When the muscle is attached to either needle or transcutaneous electrodes, muscle activity is measured by electrical frequencies sent to the Electromyograph, which can then convert these raw frequencies into several types of electromyograms (EMGs). One common type of electromyogram is called an Integrated Power Spectrum. This graphically presents the number of motor units actively contracting in the muscle over time and is measured in millivolts. The greater the number of motor units contracting at any one time indicates a stronger muscle contraction.

Figure 5:
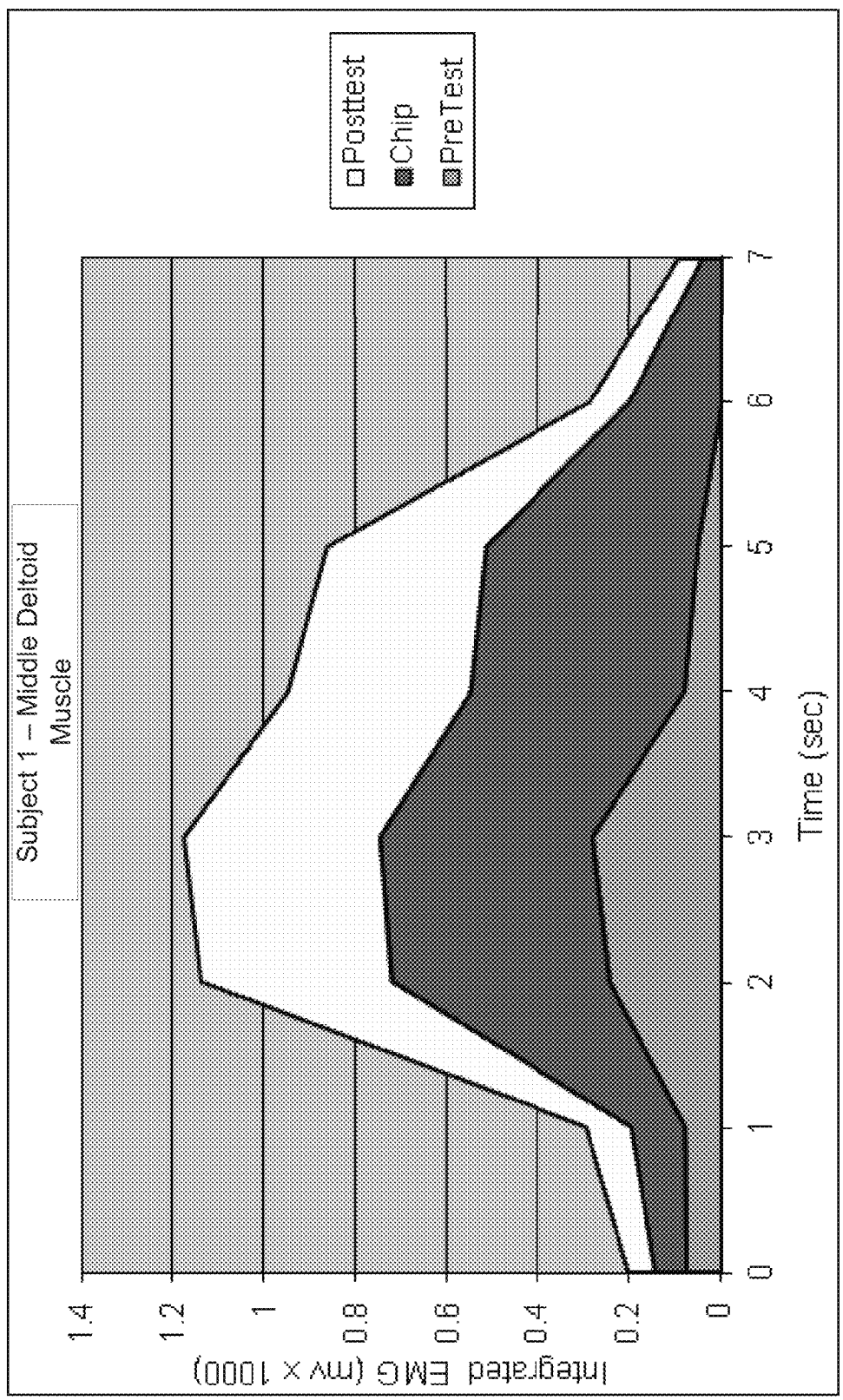
FIG. 5 is a graphical representation of data obtained during proof-of-concept testing showing improvements in muscle function.
Figure 6:
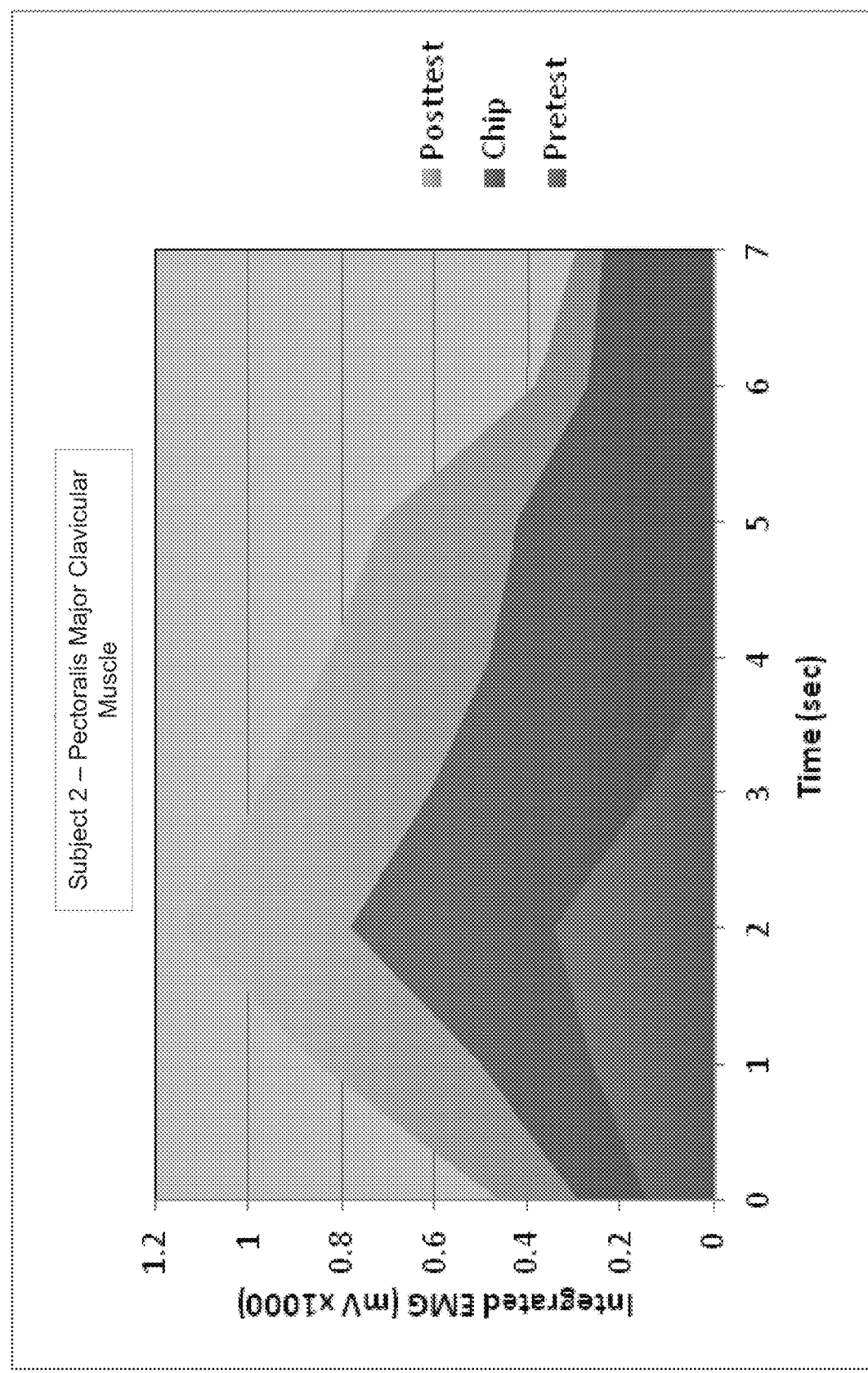
FIG. 6 is another graphical representation of data obtained during proof-of-concept testing showing improvements in muscle function.

FIGS. 5 and 6 are graphical examples of muscle testing for two different muscles conducted in preliminary human pilot studies. In these examples, the subject's muscles became "unlocked" when manually tested, and the muscles could only facilitate a small number of motor units when tested; accordingly the muscles failed under only moderate pressure applied to the corresponding limbs of the muscles. In both examples the muscles were under-facilitated because not enough motor units could fire to fully facilitate the muscle and "lock". As shown, the muscles tested were a middle deltoid muscle (FIG. 5) and a pectoralis major clavicular muscle (FIG. 6). The PreTest data (the PreTest referenced in the legends of the graphs of FIGS. 5 and 6) reflects the states of the muscles when initially evaluated.

In the Chip test (the Chip referenced in the legends of the graphs), the device 10 was applied to the navel, and the arm moved into the test position, where its fibers were aligned and shortened to provide maximal mechanical advantage during the test. With both muscles there was a dramatic increase in the number of motor units recruited (activated) by the pressure applied to the arm to "lock" the muscle and hold it in place throughout the 5 to 6-second duration of the muscle test while the device 10 was applied to the navel. As shown in the test data, there was a rapid increase in the EMG power spectra of both muscles as pressure was applied, then sustained full 5 to 6 seconds pressure was applied, and then the rapid return to baseline once the pressure had ceased.

The device 10 was removed from the navel, and after a 3 to 5 minute rest period, the muscle was tested once again, (this later test referenced as the Posttest in the legends of the graphs). As shown, both muscles recruited even a larger number of motor units than when the device 10 was being applied to navel. The Posttest data indicates that the muscles developed a full "lock" signifying a "reset" of the proprioceptors that had been inhibiting these muscles before the treatment.

Figure 7:
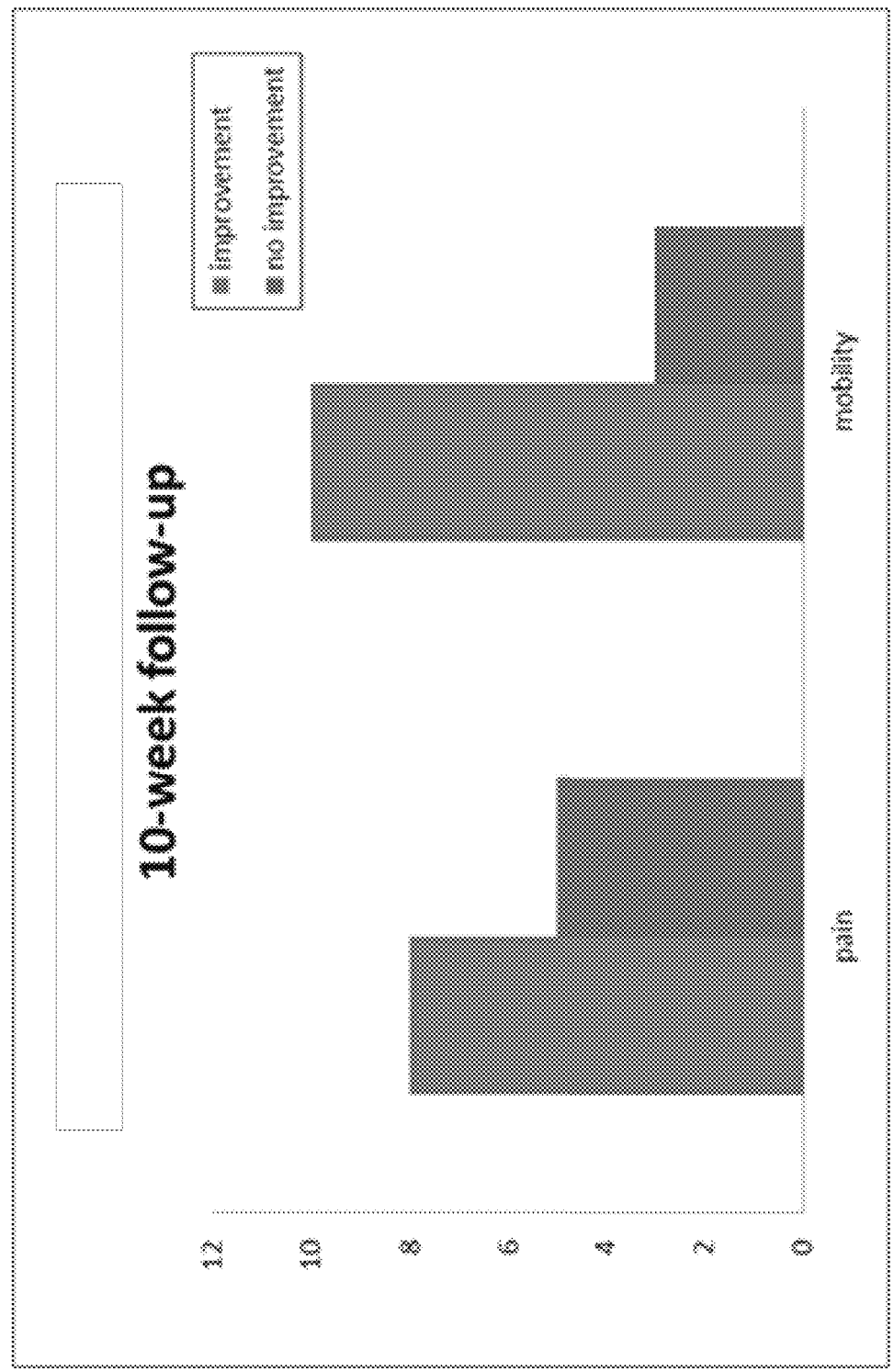
FIG. 7 is another graphical representation of data obtained during proof-of-concept testing showing improvements in pain and mobility after an extended period of time.

Referring to FIG. 7, this figure indicates that the effects from application of the device 10 in a treatment appear to be long-lasting. In this Figure, the y-axis represents a range of mobility and a pain scale in which 0 represents a state in which there is no mobility or no pain, and 10 represents a state in which there is full mobility or maximum pain. This figure reflects data obtained in a proof of concept study of a group of 13 individuals with chronic shoulder pain and muscle dysfunction who were treated only one time, yet this study group showed a greater than 77% increase in limb mobility (measured as a function of a mobility scale from 1-10). The study group also showed a nearly 62% reduction in pain ten weeks after treatment (measured as a function of a pain scale from 1-10). As indicated in the graph of FIG. 7, dark bars (left) represent patients that showed improvement for pain and mobility, while the lighter bars (right) represent those patients that did not show measurable or appreciable improvement. The graph of FIG. 7 clearly shows that 45 patients did show improvement, particularly in mobility.

In summary, the device and method of the present invention are capable of producing rapid improvement in muscle dysfunction. The therapeutic benefits can be realized by evaluating a starting point in which a muscle is in a state of overt imbalance, and is transferred to a new state of homeostasis in only 5 to 18 seconds. Many of these rapid corrections were evaluated as long-lasting.

The invention now being generally described will be more readily understood by reference to the following example, which is included merely for the purposes of illustration of certain aspects of the embodiments of the present invention. The example is not intended to limit the invention, as one of skill in the art would recognize from the above teachings and the following examples that other techniques and methods can satisfy the claims and can be employed without departing from the scope of the claimed invention.

Examples

This example provides an IRB-approved university study demonstrating the effect of a muscle optimization (MO) device of the present invention on the ability of the muscle to produce force and surface muscle energy activity. The muscle optimization device is postulated to improve muscle function by resetting muscle proprioception and improving muscle strength. Preliminary pilot studies using surface electromyography (EMG), described above, provided sufficient positive results to warrant a full-protocol study with human subjects using both EMG and a force gauge meter to test consistency and correlation.

The study is a Test-Retest design wherein the initial state of muscle imbalance was assessed with quantitative surface EMG. The muscle optimization device was applied over light clothing on the navel. The muscle with identified weakness was then activated, and force applied during testing the muscle was determined by a multi-directional force transducer, and the muscle response quantified using surface EMG. The results were analyzed for correlation between the objective force applied and the number of motor units recruited during each test. The major outcome measures are peak force generated and surface EMG curve produced during isometric or eccentric muscle contractions.

Study subjects were selected from healthy, active athletes participating in a variety of sports such as volleyball, tennis, racquetball, basketball, soccer, ice hockey, rock climbing, boxing, football, lacrosse or Nordic skiing. Participants were selected based on self-reports as being physically healthy, but who experienced muscle weakness in certain muscles/muscle groups, such as muscle imbalances of the shoulder joint: supraspinatus; middle deltoid; anterior deltoid; pectoralis major; clavicular division or latissimus dorsi. Study subjects were between the ages of 18 to 35, reportedly in good health, with no acute shoulder injury, inflammation or pain. Those subjects who reported a degenerative muscle condition or neurologic disease, such as multiple sclerosis, or asthma, were excluded from the study.

Inclusion Criteria for the test subjects: To address the inherent variability of muscle function, the study was limited to volunteer subjects who have an imbalance or weakness in one or more of the following, easily isolatable muscles of the shoulder joint.

1. supraspinatus
2. middle deltoid
3. anterior deltoid
4. pectoralis major, clavicular division
5. latissimus dorsi These muscles have been selected upon the basis of being accessible to attach the surface EMG electrodes, and agonists that can be isolated with respect to muscle fiber alignment and have limited synergist activity until relatively higher force has been applied. These are also all muscles for which multiple-examiner reliability is high. Age: between the ages of 18 to 35 Sex: male or female Health Status: self-reported in good health, Sport: subjects will be active in a sport or training that may lead to over use or misuse of shoulder muscles, specifically: volleyball, tennis, racquetball, basketball, soccer, ice hockey, rock climbing, Nordic skiing, martial arts, crew.

Exclusion Criteria for the test subjects: Chronic illness or injury: Self-reported chronic shoulder problems; a degenerative muscle or neurologic disease such as Multiple Sclerosis or asthma. Previous injuries, including acute shoulder injury, including inflammation or pain. Neck, whiplash, or spinal column injury(s); Past Surgeries: A subject having undergone any past surgeries on arm, shoulder or neck.

Subjects read and completed an Informed Consent Form in addition to a verbal description of the experiment. Those subjects participating in the study underwent muscle testing to identify inhibited/weak selected upper body muscles. Identification of muscle inhibition or weakness was assessed by placing the subject's arm in the test position and then asking the subject to "hold" against a pressure applied by the experimenter via the held-hand force transducer. The outcome of the test was scored on a qualitative+3 Scale and assigned a score of 1, 2 or 3. The direction of the pressure applied by the experimenter (e.g. "hold" your arm up with the thumb turned downward, or "hold" your arm into your side, etc., will varied depending upon which muscle was being tested. Those subjects scoring a "3" on the muscle test were assigned to the control group, subjects scoring a "1" or a "2" were assigned to the experimental group. Surface EMG electrodes were placed on the surface of the skin over the inhibited/weak muscle (for the experimental group subject), and over a standard muscle for the control group, using standard electrode placement procedures. Replicate tests were carried out on each muscle selected for assessment in the following sequence:

1) Control Test: Assessment of the initial muscle imbalance for 6 seconds (3 trials);
2) MO Device Test: Assessment of the muscle response with the MO Device placed on clothing above the navel and the muscle activated for 6 seconds (3 trials),
3) The Post-MO Device Test: Assessment of the muscle response following MO Chip therapy with no Chip on the body for 6 seconds (3 trials).

The amount of pressure was recorded using a hand-held force transducer applied by the experimenter and the EMG signal was recorded from the surface electrodes. Testing time for each subject is estimated to be no longer then one hour.

Testing Protocol and preparation of selected muscles for Surface Electromyography (EMG): Muscles that have met the inclusion criteria (either a weak muscle or a control muscle) were prepared for surface EMG recording and attached to the EMG to insure a good signal to noise ratio. The BioNomadix™ wireless EMG system (BioPac Inc.) is used to collect the muscle activity data. First, the skin is cleaned using an alcohol pad and the electrodes (EL500, BioPac Inc) are affixed to the surface of the skin above the belly of the muscle of interest. The ground electrode is affixed to an area without muscle activity.

The force transducer (microFET2) is turned on using the on/off switch, and sensitivity setting set to high. The data recording software, ErgoPak, is launched on the PC, and the meter linked via the blue tooth dongle with the software.

Muscle Test Position: The muscle(s) selected for monitoring are placed in their prescribed muscle testing position to reduce synergist(s) recruitment and to isolate the chosen muscle as much as possible as the Prime Mover or PM for that specific action. The arm is placed into the specific test position in maximal concentric contraction to align the muscle fibers of the Prime Mover, and reduce recruitment of its synergist(s). The subject is asked to "hold" their arm in this position and informed by the monitor exactly how and in which direction pressure will be applied. The subject is then asked to "hold" as the monitor begins to slowly apply increasing pressure in the test direction over approximately 2 seconds, and if the muscle "locks" to maintain that pressure for 2 seconds, then slowly release the pressure applied over approximately 2 seconds. The pressure applied is an appropriate force for the muscle tested. With this appropriate force, a clear "Lock" or "Unlock" is observed, and the results recorded. The test is repeated three times to obtain mean values for each muscle tested.

Muscle Optimization Device (MO) Procedure: Muscles that "unlocked" in the screening testing, and the control muscle were re-tested after a Muscle Optimization Chip was placed on top of clothing above subject's navel, and the triplicate testing repeated, as described above. Force—time record, surface EMG time record and peak force were recorded. Rating of muscle function (1, 2 or 3) by tester was recorded.

Muscle Optimization Device (MO) Re-Test Procedure: The MO was taken off and the muscle was re-tested in the triplicate testing procedure described above. Three to five minutes were given between the initial testing and the subsequent MO trials. Electrodes only remained affixed to the surface of a subject's skin for less than or equal to one hour in time.

A within-subject ANOVA was used to determine significant differences between conditions in terms of the maximum pressure exerted, the trial-to-trial variation in the pressure exerted, the mean peak EMG signal, and the root mean square of the EMG signal. The surface EMG results were presented graphically for each test condition, without the MO Device and with the MO Device on the navel.

Figure 8:
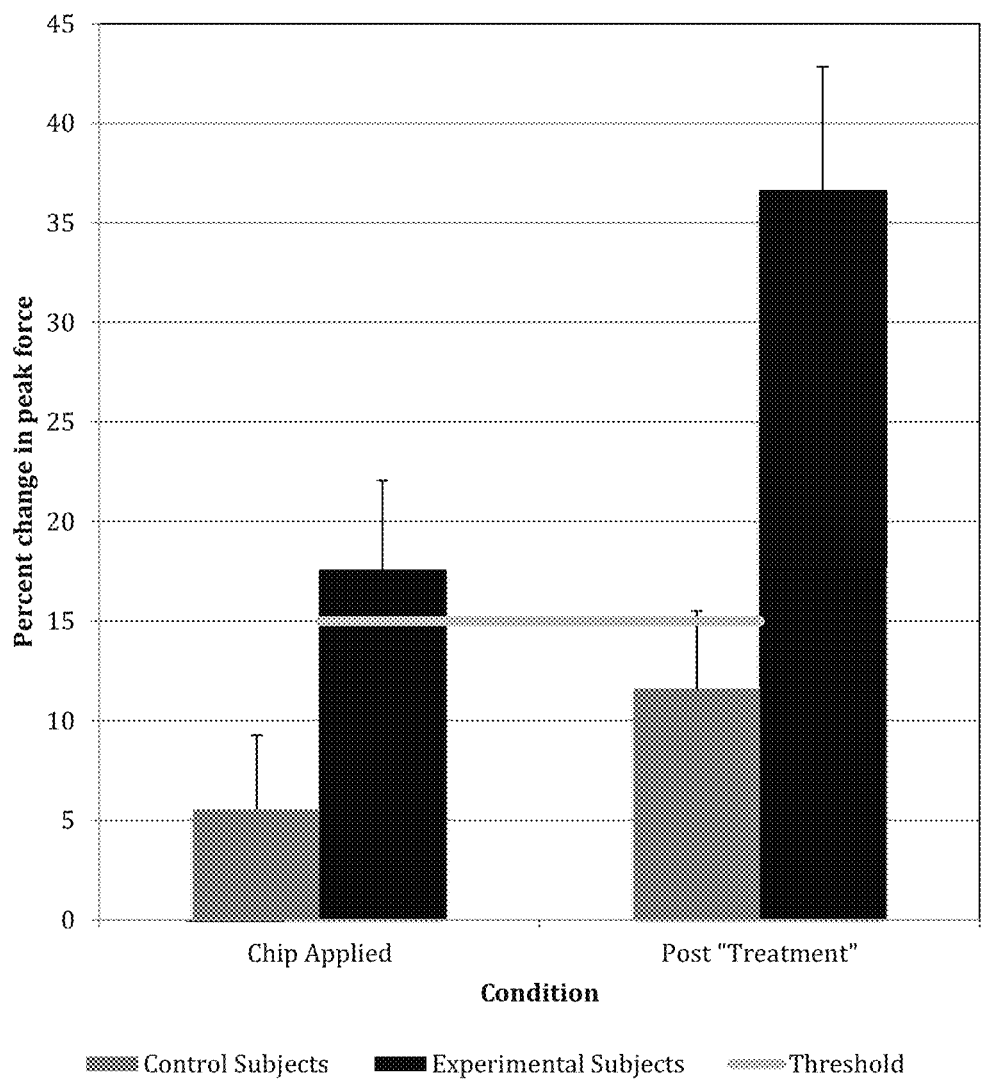
FIG. 8 shows the percentage change in peak force observed between the test conditions, results from the interim analysis of the Pilot Study described in the Examples section of this disclosure. A significant difference was observed in change in peak force between experimental and control subjects, $p<0.05$. Additionally, the Threshold represents a meaningful change in force, based upon published literature.
Figure 9:
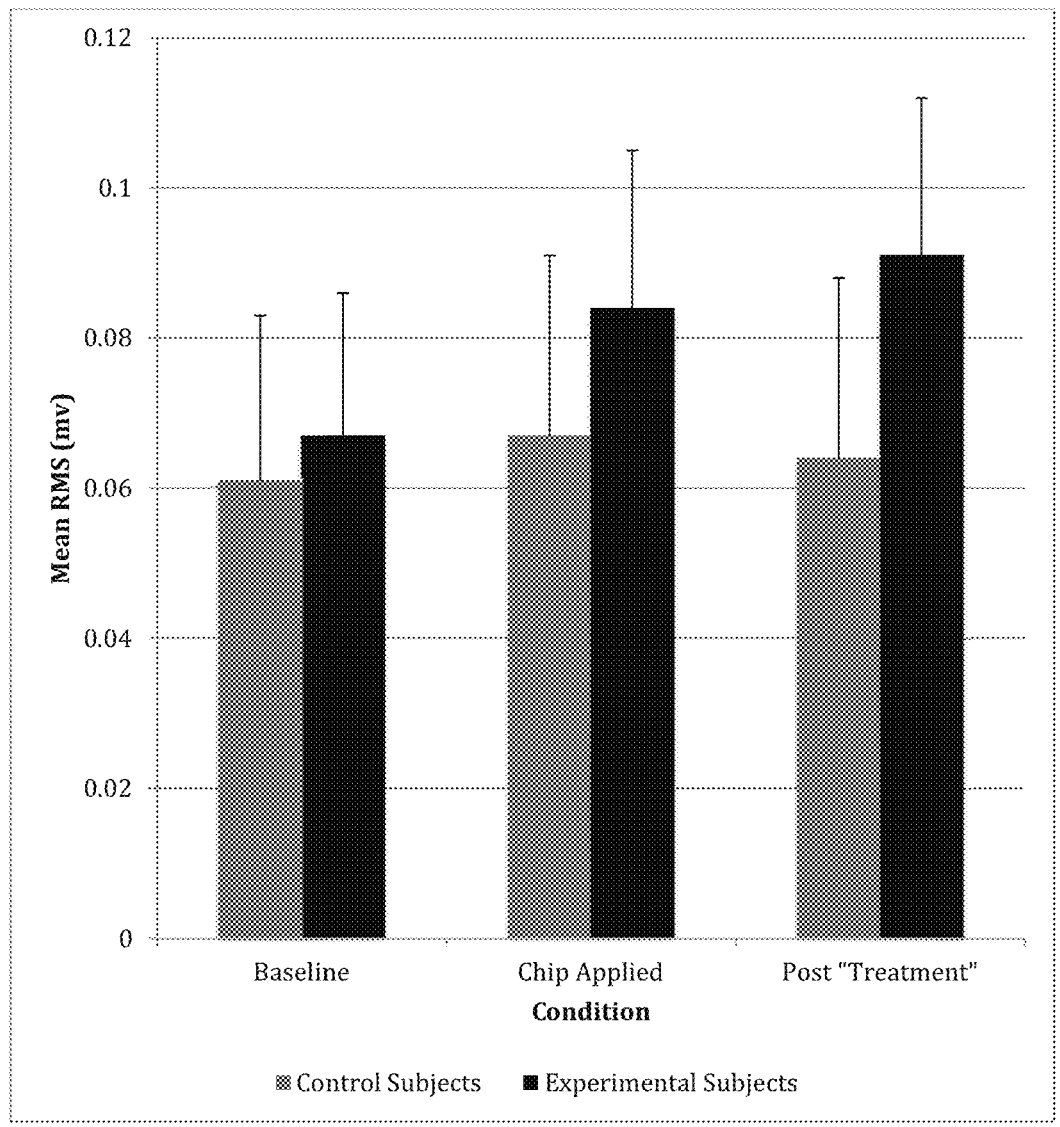
FIG. 9 shows the mean EMG Root Mean Square for the three test conditions, results from the interim analysis of the Pilot Study described in the Examples section of this disclosure. A significant difference was observed between Chip Applied and Post "Treatment" for Experimental Subjects, $p<0.05$.
Figure 10:
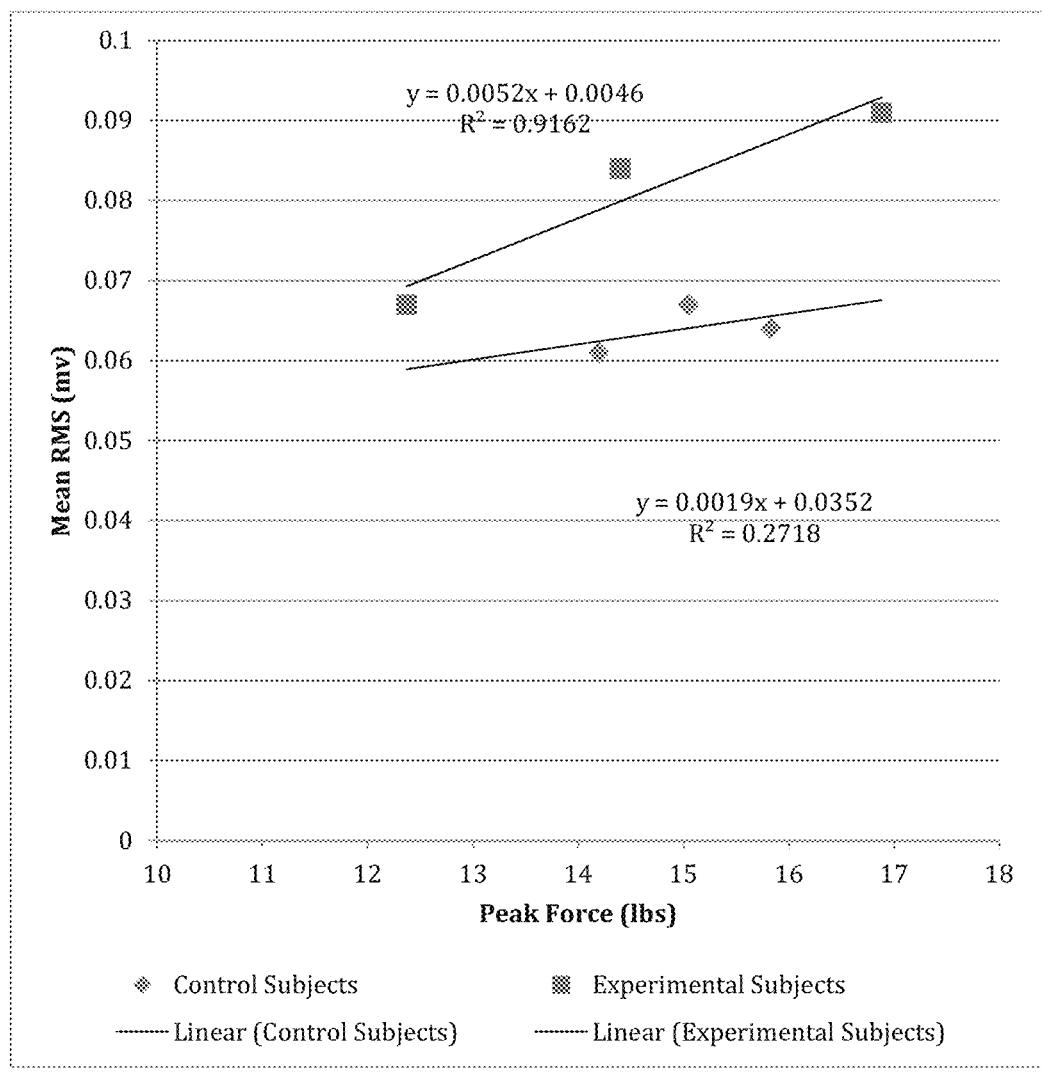
FIG. 10 shows the relationship between the peak force and the mean EMG Root Mean Square for the three test conditions, results from the interim analysis of the Pilot Study described in the Examples section of this disclosure. A reasonable linear relationship was observed for peak force and mean EMG RMS.
Figure 11:
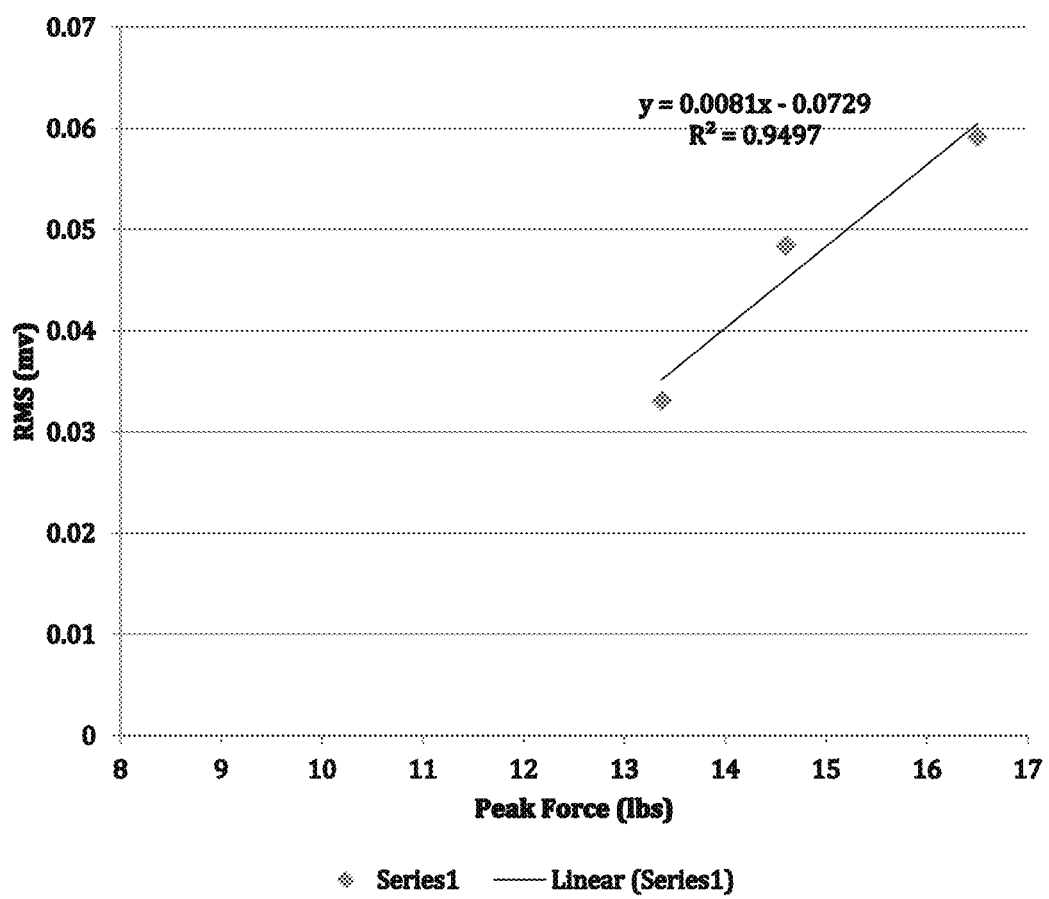
FIG. 11 shows an example of an individual relationship between the peak force and the mean EMG Root Mean Square for the three test conditions, experimental subject 10, anterior deltoid muscle, results from the interim analysis of the Pilot Study described in the Examples section of this disclosure.

Results: As shown in FIG. 8, with interim results from n=14 subjects tested in this Pilot Study, a significant difference has been observed in change in peak force between experimental and control subjects ($p<0.05$). Additionally, the threshold represents a meaningful change in force, based upon published literature. As shown in FIG. 9, a significant difference was observed in the mean EMG Root Mean Square for the three test conditions between Chip Applied and Post "Treatment" for experimental Subjects ($p<0.05$). As shown in FIG. 10, a reasonable linear relationship was observed for peak force and mean EMG Root Mean Square (RMS) for the three test conditions. FIG. 11 provides an example of the relationship between the peak force and the mean EMG Root Mean Square (RMS) for the three test conditions in a single experimental subject, anterior deltoid muscle.

In other embodiments of the invention, the substrate or carrier layer 12 comprises a resonance frequency or resonance frequencies that are used in applications of the device 10. In these embodiments, the carrier layer 12 and its resonance frequency or frequencies may be utilized in tandem with the mineral matrix layer 14 and its resonance frequency or frequencies, or the carrier layer 12 may stand alone. In other words, the device 10 may optionally include the carrier layer 12 on the mineral matrix layer 14 along with a delivery mechanism to generate the therapeutic benefits of the invention.

The size and shape of a carrier layer 12 at least partially determines the resonance frequency of the carrier layer 12, and the range of frequencies that the carrier layer 12 is capable of generating. For example, when the carrier layer 12 is a crystal, the crystal may comprise a particular cut that influences the crystal's resonance frequency as well as how environmental qualities such as temperature, pressure, humidity, and vibrations impact the performance of the crystal. Examples of crystal cuts include, but are not limited to, AT, SC, BT, IT, FC, AK, CT, DT, SL, GT, E, 5°X, MT, ET, FT, NT, XY, H, J, RT, SBTC, TS, X 30°, LC, AC, BC, NLSC, Y, X, and combinations thereof.

The material that the carrier layer 12 is made from also at least partially determines the resonance frequency of the carrier layer 12, and the range of frequencies that the carrier layer 12 is capable of generating. The carrier layer 12 may be comprised of a variety of materials including, but not limited to, piezoelectric crystal, quartz, silicon, plastic, glass, saline solution, synthetic crystal, sapphire, moissanite, natural crystal, gem stone, metal, ceramic, resin, viscous substance, lithium tantalate, lithium niobate, lithium borate, berlinite, gallium arsenide, lithium tetraborate, aluminium phosphate, bismuth germanium oxide, polycrystalline zirconium titanate ceramics, high-alumina ceramics, silicon-zinc oxide composite, dipotassium tartrate, gallium phosphate, langasite, langanite, langanate, and combinations thereof.

In some embodiments of the present invention the carrier layer 12 is resonance inert, meaning the carrier layer 12 does not comprise a resonance frequency. These carrier layers 12 may simply provide a substrate for the mineral matrix layer 14. For example, a silicon wafer grown by the Czochralski method adds no characteristic resonance frequencies beyond its natural phonon frequencies.

Delivery mechanisms that excite frequency responses according to the invention utilize electromagnetic or mechanical waves, wherein mechanical waves include acoustic waves generated by devices such as a piezoelectric transducer and other similar devices. In some embodiments, an acoustic resonator such as a tuning fork may have a frequency range between approximately 62 Hz and 4111 Hz, wherein the tuning fork may excite a resonance frequency in a layer. Other delivery mechanisms may produce ultrasonic waves, which are acoustic waves above the range of normal human hearing.

In the realm of electromagnetism, the source of the electric field may come from a variety of electromagnetic delivery mechanisms. For example, frequency generators, Pulsed Electromagnetic Fields ("PEMF"), Transcutaneous Electrical Nerve Stimulation ("TENS"), LASERs, and other similar devices can be used as a delivery mechanism to excite a frequency response in the device 10.

Frequency generators may control the wave frequency, wave form, and wave amplitude among other attributes of electromagnetic waves. In a specific example, a FG085 MiniDDS Function Generator is connected to a sheet or membrane with alligator clips or other means of operative connection. The membrane in this embodiment has piezoelectric properties, meaning electric charge accumulates in response to mechanical stress, or vice versa. A particular frequency, wave form, and amplitude may be applied to the membrane to alter the electromagnetic properties of the membrane, for example, to match the electromagnetic signal of nutraceuticals or other bodily components. After an embedding step, the membrane may be used as the substrate or carrier layer 12 or may be added in combination with any layer of the device 10.

PEMF devices emit pulsations of electromagnetic radiation. The pulse wave or rectangular wave form is the preferred wave form associated with PEMF delivery mechanisms. However, PEMF delivery mechanisms may also utilize sine waves, square waves, triangle waves, sawtooth waves, or any other waveform commonly known in the art. Other important parameters associated with the PEMF delivery mechanism include the frequency of the electromagnetic radiation and the amplitude of the electromagnetic radiation. PEMF delivery mechanisms used in combination with devices 10 described elsewhere herein can be used to treat pain, including chronic pain. Further literature regarding the benefits of PEMF treatment may be found in Rheumatol Int (2010) 30:571-586; Alternative Therapies, July/August (2003), Vol. 9 No. 4, 38-48; and Cell Biochem Biophys (2013) 67:1229-1237, which are incorporated herein in their entirety by reference.

For the PEMF delivery mechanism and other delivery mechanisms that utilize electromagnetic radiation, a variety of frequencies may be utilized. For example, radio waves (3 Hz-300 MHz), microwaves (300 MHz-300 GHz), infrared waves (300 GHz-400 THz), visible light (400 THz-770 THz), ultraviolet light (770 THz-30 PHz), X-rays (30 PHz-30 EHz), and gamma rays (more than 30 EHz) are all frequencies that the electromagnetic delivery mechanisms may utilize. Typically, lower frequencies are preferred in the utilization of PEMF devices as a delivery mechanism. In some embodiments, the PEMF delivery mechanism produces a frequency less than approximately 3,000 Hz. In further embodiments, the PEMF delivery mechanism produces a frequency less than approximately 100 Hz. In yet further embodiments, the PEMF delivery mechanism produces a frequency less than approximately 24 Hz.

In one embodiment, a substrate or carrier layer 12 and/or a mineral matrix layer 14 may be embedded with frequencies that correspond with the natural resonance of oxygen molecules, which typically ranges between 57 and 64 GHz. Further, the carrier layer 12 and/or mineral matrix layer 14 may be excited with these frequencies. An oxygen-specific carrier layer 12 or mineral matrix layer may be used in combination with other layers described elsewhere herein.

Further, a frequency sweeping option may be utilized with electromagnetic delivery mechanisms. In one embodiment, the frequency sweep occurs between a first and a second reference frequency over a period of time. In some embodiments, the reference frequencies are approximately 0.5 Hz and 32 kHz. Reference frequencies may also include Schumann resonances (7.83 Hz and harmonics thereof, including 14.3, 20.8, 27.3, and 33.8 Hz). Further, reference frequencies can include any frequency of the electromagnetic spectrum. The frequency sweep occurs over time, but the sweep is not necessarily a continuous sweep between two reference frequencies. For example, a delivery mechanism may emit a first reference frequency for a first time period, and second reference frequency for a second time period, a third reference frequency for a second time period, and so on. One skilled in the art will appreciate various combinations of references frequencies and time periods to implement a frequency sweep option for a delivery mechanism.

One particular example of a PEMF is a device which pulses DC current to produce a pulsed electric field. This is significant because the coil applicator can be turned to provide predominately positive or predominately negative fields to the body. Using approximately 160 volts, it is possible to pulse electromagnetic waves with a frequency less than 20 kHz.

Next, TENS delivery mechanisms utilize an electric current for nerve stimulation. TENS devices may modulate the pulse width, frequencies, amplitude, wave form, etc. of electromagnetic waves. Generally TENS is applied at high frequency (>50 Hz) with an intensity below motor contraction (sensory intensity) or low frequency (<10 Hz) with an intensity that produces motor contraction. Typically, the TENS devices includes one or more electrodes to deliver the electromagnetic wave. Dermal patches may be incorporated to adhere the electrode to a portion of a user's skin such that electrode is fixed relative to a muscle or muscle group. One skilled in the art will appreciate that a patch or other similar device may be used with other delivery mechanisms such as the PEMF device to secure the delivery mechanism relative to the muscle or muscle group.

In one particular example of the present invention, the carrier layer 12 is a quartz crystal with a particular size and cut. A quartz crystal has piezoelectric properties wherein an electric field distorts the physical shape of the quartz crystal. When the electric field is altered the quartz crystal changes shape and generates an electric field of its own. The rate of expansion and contraction of the quartz crystal can be the resonance frequency or resonance frequencies of the carrier layer 12.

In some embodiments of the present invention, the portion of the device 10, a carrier layer 12 and/or a mineral matrix layer 14, that comprises a resonance frequency may be heated or cooled to affect the performance of the layer 12, 14. In one embodiment, the carrier layer 12 comprises a resonance frequency. The carrier layer 12 may be heated or cooled when the carrier 12 is placed in proximity to the muscle or muscle group, and the delivery mechanism is placed in proximity to the carrier layer 12. Depending on attributes of the carrier layer 12 such as the cut, the change in temperature can affect the frequencies generated by the excitation of the carrier layer 12, and the change in temperature can directly enhance the therapeutic on the user.

Although the present disclosure describes components and functions implemented in the aspects, embodiments, and/or configurations with reference to particular standards and protocols, the aspects, embodiments, and/or configurations are not limited to such standards and protocols. Other similar standards and protocols not mentioned herein are in existence and are considered to be included in the present disclosure.

The present disclosure, in various aspects, embodiments, and/or configurations, includes components, methods, processes, systems and/or apparatus substantially as depicted and described herein, including various aspects, embodiments, configurations embodiments, subcombinations, and/or subsets thereof. Those of skill in the art will understand how to make and use the disclosed aspects, embodiments, and/or configurations after understanding the present disclosure. The present disclosure, in various aspects, embodiments, and/or configurations, includes providing devices and processes in the absence of items not depicted and/or described herein or in various aspects, embodiments, and/or configurations hereof, including in the absence of such items as may have been used in previous devices or processes, e.g., for improving performance, achieving ease and\or reducing cost of implementation.

The foregoing discussion has been presented for purposes of illustration and description. The foregoing is not intended to limit the disclosure to the form or forms disclosed herein. In the foregoing Detailed Description for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for treatment of biological tissue by application of therapeutic frequency patterns, said method comprising:
    providing a therapeutic frequency resonance pattern device, said device comprising a substrate layer and a mineral matrix layer having at least one resonance frequency imbedded therein;
    placing said device in proximity to a muscle of a patient;
    providing a delivery mechanism in proximity to said device;
    exciting said at least one resonance frequency of said mineral matrix layer using a wave produced by said delivery mechanism, said wave comprising at least one of a mechanical wave and an electromagnetic wave; and
    removing said device from proximity with the patient.

2. The method, as claimed in claim 1, wherein:
    said wave comprises a waveform that is at least one of a sine wave, a square wave, a triangle wave, and a sawtooth wave.

3. The method, as claimed in claim 1, wherein:
    said substrate layer of said device comprises one of piezoelectric crystal, quartz, silicon, plastic, glass, saline solution, synthetic crystal, sapphire, moissanite, natural crystal, gem stone, ceramic, viscous substance, lithium tantalate, lithium niobate, lithium borate, berlinite, gallium arsenide, lithium tetraborate, aluminium phosphate, bismuth germanium oxide, polycrystalline zirconium titanate ceramics, high-alumina ceramics, silicon-zinc oxide composite, dipotassium tartrate, gallium phosphate, langasite, langanite, langanate, and combinations thereof.

4. The method, as claimed in claim 1, wherein:
    said device further comprises a protective layer placed over said mineral matrix layer.

5. The method, as claimed in claim 1, wherein:
    said substrate layer comprises a crystal cut, wherein said crystal cut is at least one of AT, SC, BT, IT, FC, AK, CT, DT, SL, GT, E, 5°X, MT, ET, FT, NT, XY, H, J, RT, SBTC, TS, X 30°, LC, AC, BC, NLSC, Y, X, and combinations thereof.

6. The method, as claimed in claim 1, wherein:
    said delivery mechanism produces said wave through a range of frequencies.

7. The method, as claimed in claim 6, wherein:
    said range of frequencies is between 7.83 Hz to 33.8 Hz.

8. The method, as claimed in claim 1, wherein:
    said delivery mechanism includes at least one of an acoustic resonator, a frequency generator, a Pulsed Electromagnetic Field ("PEMF") device, a Transcutaneous Electrical Nerve Stimulation ("TENS") device, and a LASER device.

9. The method, as claimed in claim 8, wherein:
    said acoustic resonator includes a tuning fork having a frequency range between 62 Hz and 4111 Hz.

10. The method, as claimed in claim 8, wherein:
said PEMF device produces a pulsed electric field to generate said electromagnetic wave, and wherein said electromagnetic wave has a frequency less than 20 KHz.

11. A method for treatment of biological tissue by application of therapeutic frequency patterns, said method comprising:
providing a therapeutic frequency resonance pattern device, said device comprising a substrate layer and a mineral matrix layer having at least one resonance frequency imbedded therein, said substrate layer comprising one of a piezoelectric crystal, quartz, silicon, crystal cut, synthetic crystal, and combinations thereof;
placing said device in proximity to a muscle of a patient;
providing a delivery mechanism in proximity to said device;
exciting said at least one resonance frequency of said mineral matrix layer using a wave produced by said delivery mechanism at a desired frequency, said wave comprising at least one of a mechanical wave and an electromagnetic wave; and
removing said device from proximity with the patient.

12. The method, as claimed in claim 11, wherein:
said wave comprises a waveform that is at least one of a sine wave, a square wave, a triangle wave, and a sawtooth wave.

13. The method, as claimed in claim 11, wherein:
said device further comprises a protective layer placed over said mineral matrix layer.

14. The method, as claimed in claim 11, wherein:
said delivery mechanism produces said wave through a range of frequencies.

15. The method, as claimed in claim 11, wherein:
said delivery mechanism includes at least one of an acoustic resonator, a frequency generator, a Pulsed Electromagnetic Field ("PEMF") device, a Transcutaneous Electrical Nerve Stimulation ("TENS") device, and a LASER device.

16. A system for treatment of biological tissue by application of therapeutic frequency patterns, said system comprising:
a therapeutic frequency resonance pattern device, said device comprising a substrate layer and a mineral matrix layer having at least one resonance frequency imbedded therein, said device adapted to be placed proximate to the biological tissue to be treated;
a delivery mechanism located in proximity to said device to produce a wave that excites said at least one resonance frequency of said mineral matrix layer to therefore provide therapeutic benefits to said biological tissue; and
wherein said delivery mechanism includes at least one of an acoustic resonator, a frequency generator, a Pulsed Electromagnetic Field ("PEMF") device, a Transcutaneous Electrical Nerve Stimulation ("TENS") device, or a LASER device.

17. The system, as claimed in claim 16, wherein:
said wave comprises at least one of a mechanical wave and an electromagnetic wave.

18. The system, as claimed in claim 16, wherein:
said wave comprises a waveform, wherein said waveform is at least one of a sine wave, a square wave, a triangle wave, and a sawtooth wave.

19. The system, as claimed in claim 16, wherein:
said substrate layer of said therapeutic frequency resonance pattern device comprises one of piezoelectric crystal, quartz, silicon, plastic, glass, saline solution, synthetic crystal, sapphire, moissanite, natural crystal, gem stone, ceramic, viscous substance, lithium tantalate, lithium niobate, lithium borate, berlinite, gallium arsenide, lithium tetraborate, aluminium phosphate, bismuth germanium oxide, polycrystalline zirconium titanate ceramics, high-alumina ceramics, silicon-zinc oxide composite, dipotassium tartrate, gallium phosphate, langasite, langanite, langanate, and combinations thereof.

20. The system, as claimed in claim 16, wherein:
said therapeutic frequency resonance pattern device further comprises a protective layer placed over said mineral matrix layer.

21. The system, as claimed in claim 16, wherein:
said substrate layer comprises a crystal cut, wherein said crystal cut is at least one of AT, SC, BT, IT, FC, AK, CT, DT, SL, GT, E, 5°X, MT, ET, FT, NT, XY, H, J, RT, SBTC, TS, X 30°, LC, AC, BC, NLSC, Y, X, and combinations thereof.

* * * * *